United States Patent
Frey et al.

(10) Patent No.: US 11,633,254 B2
(45) Date of Patent: Apr. 25, 2023

(54) PATIENT-MATCHED APPARATUS FOR USE IN AUGMENTED REALITY ASSISTED SURGICAL PROCEDURES AND METHODS FOR USING THE SAME

(71) Applicant: Mighty Oak Medical, Inc., Englewood, CO (US)

(72) Inventors: George Frey, Englewood, CO (US); Caleb Voelkel, Lakewood, CO (US); Adam Jensen, Golden, CO (US); Sean Starkman, Centennial, CO (US)

(73) Assignee: Mighty Oak Medical, Inc., Englewood, CO (US)

( * ) Notice: Subject to any disclaimer, the term of this patent is extended or adjusted under 35 U.S.C. 154(b) by 605 days.

(21) Appl. No.: 16/831,215

(22) Filed: Mar. 26, 2020

(65) Prior Publication Data

US 2020/0360105 A1    Nov. 19, 2020

Related U.S. Application Data

(63) Continuation-in-part of application No. 16/598,861, filed on Oct. 10, 2019, now Pat. No. 11,376,073,
(Continued)

(51) Int. Cl.
*A61B 90/00*      (2016.01)
*A61B 17/88*      (2006.01)
(Continued)

(52) U.S. Cl.
CPC .............. *A61B 90/36* (2016.02); *A61B 17/88* (2013.01); *A61B 17/90* (2021.08); *A61B 34/76* (2016.02);
(Continued)

(58) Field of Classification Search
CPC ......... A61B 90/36; A61B 17/88; A61B 17/90; A61B 34/76; A61B 2017/00203;
(Continued)

(56) References Cited

U.S. PATENT DOCUMENTS

| 3,151,392 A | 10/1964 | Chambers |
| 5,201,734 A | 4/1993 | Cozad et al. |

(Continued)

FOREIGN PATENT DOCUMENTS

| CA | 2736525 | 3/2010 |
| CA | 2862341 | 8/2013 |

(Continued)

OTHER PUBLICATIONS

Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.
(Continued)

*Primary Examiner* — Sanjay Cattungal
(74) *Attorney, Agent, or Firm* — FisherBroyles LLP; Ian R. Walsworth

(57) ABSTRACT

The present disclosure relates to systems and methods for robotic, computer-aided or virtual/augmented reality assisted procedures, including with use a of patient-specific or patient-matched, customized apparatus for assisting in various surgical procedures. In varying embodiments, patient-specific guides may comprise embedded markers, chips, circuits, or other registerable components for providing information to a robotic or computer-aided device. Other apparatus described herein may be aligned and/or matched with the robotic or augmented reality equipment or another apparatus during a surgical procedure.

25 Claims, 18 Drawing Sheets

Related U.S. Application Data which is a continuation-in-part of application No. 15/997,404, filed on Jun. 4, 2018, now Pat. No. 11,039,889.

(60) Provisional application No. 62/823,911, filed on Mar. 26, 2019, provisional application No. 62/743,661, filed on Oct. 10, 2018.

(51) Int. Cl.
| | | |
|---|---|---|
| A61B 34/20 | (2016.01) | |
| A61B 34/00 | (2016.01) | |
| A61B 90/50 | (2016.01) | |
| A61B 17/00 | (2006.01) | |
| A61B 17/90 | (2006.01) | |

(52) U.S. Cl.
CPC ............ *A61B 2017/00203* (2013.01); *A61B 2034/2048* (2016.02); *A61B 2090/0807* (2016.02); *A61B 2090/365* (2016.02); *A61B 2090/372* (2016.02); *A61B 2090/3916* (2016.02); *A61B 2090/3975* (2016.02); *A61B 2090/3983* (2016.02); *A61B 2090/3987* (2016.02); *A61B 2090/3995* (2016.02); *A61B 2090/502* (2016.02)

(58) Field of Classification Search
CPC .... A61B 2034/2048; A61B 2090/0807; A61B 2090/365; A61B 2090/372; A61B 2090/3916; A61B 2090/3975; A61B 2090/3983; A61B 2090/3987; A61B 2090/3995; A61B 2090/502; A61B 34/32; A61B 90/11; A61B 2034/107; A61B 17/1739; A61B 17/1757; A61B 17/7055; A61B 34/10; A61B 2017/568; A61B 2034/108; A61B 2034/2055; A61B 2090/363; A61B 90/90; A61B 34/20
See application file for complete search history.

(56) References Cited

U.S. PATENT DOCUMENTS

| | | | |
|---|---|---|---|
| D359,557 S | 6/1995 | Hayes | |
| 5,490,409 A | 2/1996 | Weber | |
| 5,527,312 A | 6/1996 | Ray | |
| 5,569,246 A | 10/1996 | Ojima et al. | |
| D403,066 S | 12/1998 | DeFonzo | |
| 5,865,846 A | 2/1999 | Bryan et al. | |
| D412,032 S | 7/1999 | Mikula-Curtis et al. | |
| 5,993,453 A | 11/1999 | Bullara et al. | |
| 6,006,581 A | 12/1999 | Holmes | |
| D420,132 S | 2/2000 | Bucholz et al. | |
| 6,030,401 A | 2/2000 | Marino | |
| 6,035,691 A | 3/2000 | Lin et al. | |
| 6,063,088 A | 5/2000 | Winslow | |
| D428,989 S | 8/2000 | Segermark et al. | |
| 6,113,602 A | 9/2000 | Sand | |
| 6,142,998 A | 11/2000 | Smith et al. | |
| 6,221,077 B1 | 4/2001 | Rinner et al. | |
| 6,290,724 B1 | 9/2001 | Marino | |
| 6,309,395 B1 | 10/2001 | Smith et al. | |
| 6,328,738 B1 | 12/2001 | Suddaby | |
| 6,364,880 B1 | 4/2002 | Michelson | |
| 6,644,087 B1 | 11/2003 | Ralph et al. | |
| 6,711,432 B1* | 3/2004 | Krause ................. | A61B 90/36 |
| | | | 600/426 |
| 6,719,795 B1 | 4/2004 | Cornwall | |
| 6,755,839 B2 | 6/2004 | Van Hoeck et al. | |
| 7,014,640 B2 | 3/2006 | Kemppanien et al. | |
| 7,025,769 B1 | 4/2006 | Ferree | |
| 7,077,864 B2 | 7/2006 | Byrd, III et al. | |
| D532,515 S | 11/2006 | Buttler et al. | |
| D533,664 S | 12/2006 | Buttler et al. | |
| 7,207,992 B2 | 4/2007 | Ritland | |
| 7,235,076 B2 | 6/2007 | Pacheco | |
| 7,288,093 B2 | 10/2007 | Michelson | |
| 7,341,590 B2 | 3/2008 | Ferree | |
| 7,387,643 B2 | 6/2008 | Michelson | |
| 7,406,775 B2 | 8/2008 | Funk et al. | |
| 7,454,939 B2 | 11/2008 | Garner et al. | |
| 7,491,180 B2 | 2/2009 | Pacheco | |
| 7,559,931 B2 | 7/2009 | Stone | |
| 7,623,902 B2 | 11/2009 | Pacheco | |
| D606,195 S | 12/2009 | Eisen et al. | |
| 7,658,610 B2 | 2/2010 | Knopp | |
| D618,796 S | 6/2010 | Cantu et al. | |
| 7,844,356 B2 | 11/2010 | Matov et al. | |
| 7,955,355 B2 | 6/2011 | Cin | |
| 7,957,824 B2 | 6/2011 | Boronvinskih et al. | |
| 7,957,831 B2 | 6/2011 | Isaacs | |
| 7,967,868 B2 | 6/2011 | White et al. | |
| 8,057,482 B2 | 11/2011 | Stone et al. | |
| 8,070,752 B2 | 12/2011 | Metzger et al. | |
| 8,092,465 B2 | 1/2012 | Metzger et al. | |
| 8,118,815 B2 | 2/2012 | van der Walt | |
| 8,159,753 B2 | 4/2012 | Ojeda et al. | |
| 8,167,884 B2 | 5/2012 | Pacheco | |
| 8,175,683 B2 | 5/2012 | Roose | |
| 8,206,396 B2* | 6/2012 | Trabish ................. | A61F 2/4657 |
| | | | 606/86 R |
| 8,214,014 B2 | 7/2012 | Pacheco | |
| 8,236,006 B2 | 8/2012 | Hamada | |
| 8,241,293 B2 | 8/2012 | Stone | |
| 8,257,083 B2* | 9/2012 | Berckmans, III .... | A61C 8/0001 |
| | | | 433/213 |
| D669,176 S | 10/2012 | Frey | |
| D669,984 S | 10/2012 | Cheney et al. | |
| 8,277,461 B2 | 10/2012 | Pacheco | |
| 8,282,646 B2 | 10/2012 | Schoenefeld | |
| 8,298,235 B2 | 10/2012 | Grinberg | |
| 8,298,237 B2 | 10/2012 | Schoenefeld | |
| 8,298,242 B2 | 10/2012 | Justis et al. | |
| D672,038 S | 12/2012 | Frey | |
| 8,357,111 B2* | 1/2013 | Caillouette .......... | A61B 5/6828 |
| | | | 600/595 |
| 8,377,066 B2 | 2/2013 | Katrana et al. | |
| 8,407,067 B2 | 3/2013 | Ulthgenannt et al. | |
| 8,419,740 B2* | 4/2013 | Aram ................. | A61B 17/1764 |
| | | | 606/88 |
| D685,087 S | 6/2013 | Voic | |
| 8,460,303 B2 | 6/2013 | Park | |
| 8,480,679 B2 | 7/2013 | Park et al. | |
| 8,535,387 B2 | 9/2013 | Meridew et al. | |
| 8,540,719 B2 | 9/2013 | Peukert et al. | |
| 8,545,509 B2 | 10/2013 | Park et al. | |
| 8,549,888 B2 | 10/2013 | Isaacs | |
| 8,568,487 B2 | 10/2013 | Witt et al. | |
| 8,591,516 B2 | 11/2013 | Metzger et al. | |
| 8,603,180 B2 | 12/2013 | White et al. | |
| 8,607,603 B2 | 12/2013 | Justis et al. | |
| 8,608,748 B2 | 12/2013 | Metzger et al. | |
| 8,608,749 B2 | 12/2013 | Witt et al. | |
| 8,632,547 B2 | 1/2014 | Metzger et al. | |
| 8,668,700 B2 | 3/2014 | Catanzarite | |
| D705,929 S | 5/2014 | Frey | |
| 8,721,651 B2 | 5/2014 | Loke et al. | |
| 8,758,357 B2 | 6/2014 | Frey | |
| 8,808,302 B2 | 8/2014 | White et al. | |
| 8,808,303 B2 | 8/2014 | Stemniski et al. | |
| 8,858,561 B2 | 10/2014 | White et al. | |
| 8,864,769 B2 | 10/2014 | Stone et al. | |
| 8,870,889 B2 | 10/2014 | Frey | |
| D718,862 S | 12/2014 | Matheny | |
| D718,863 S | 12/2014 | Matheny | |
| D718,864 S | 12/2014 | Matheny | |
| 8,979,749 B2 | 3/2015 | Gorek et al. | |
| 8,992,538 B2 | 3/2015 | Keefer | |
| D726,914 S | 4/2015 | Matheny | |
| 9,017,412 B2 | 4/2015 | Wolters et al. | |
| 9,044,285 B2 | 6/2015 | Harper | |
| 9,066,727 B2 | 6/2015 | Catanzarite et al. | |

(56) References Cited

U.S. PATENT DOCUMENTS

| | | | |
|---|---|---|---|
| 9,066,816 | B2 | 6/2015 | Allard et al. |
| 9,113,971 | B2 | 8/2015 | Metzger et al. |
| D738,498 | S | 9/2015 | Frey et al. |
| 9,138,325 | B2 | 9/2015 | Mouw |
| 9,173,661 | B2 | 11/2015 | Metzger et al. |
| D745,671 | S | 12/2015 | Frey et al. |
| D745,672 | S | 12/2015 | Frey et al. |
| D745,673 | S | 12/2015 | Frey et al. |
| 9,198,678 | B2 * | 12/2015 | Frey .................. G06F 30/00 |
| 9,289,253 | B2 | 3/2016 | Sweeney |
| 9,451,973 | B2 * | 9/2016 | Heilman ............ A61F 2/4081 |
| 9,486,324 | B2 | 11/2016 | Hochschuler |
| D775,335 | S | 12/2016 | Frey et al. |
| 9,642,633 | B2 | 5/2017 | Frey et al. |
| 9,649,160 | B2 | 5/2017 | van der Walt et al. |
| 9,662,157 | B2 | 5/2017 | Schneider et al. |
| 9,675,400 | B2 | 6/2017 | Katrana et al. |
| 9,737,339 | B2 | 8/2017 | Copp et al. |
| 9,814,497 | B1 | 11/2017 | Al-Habib et al. |
| 9,826,991 | B2 | 11/2017 | Kaiser et al. |
| 9,839,448 | B2 | 12/2017 | Reckling et al. |
| 9,848,922 | B2 | 12/2017 | Tohmeh et al. |
| 9,913,669 | B1 | 3/2018 | Scholl et al. |
| 9,949,843 | B2 | 4/2018 | Reiley et al. |
| 9,968,408 | B1 | 5/2018 | Casey et al. |
| 9,987,024 | B2 | 6/2018 | Frey et al. |
| 10,085,784 | B2 | 10/2018 | Ono et al. |
| 10,166,033 | B2 | 1/2019 | Keiley et al. |
| 2004/0097925 | A1 | 5/2004 | Boehm et al. |
| 2004/0144149 | A1 | 7/2004 | Strippgen et al. |
| 2004/0243481 | A1 | 12/2004 | Bradbury et al. |
| 2005/0148843 | A1 | 7/2005 | Roose |
| 2005/0177156 | A1 | 8/2005 | Timm et al. |
| 2005/0262911 | A1 | 12/2005 | Dankowicz et al. |
| 2006/0058792 | A1 | 3/2006 | Hynes |
| 2006/0084986 | A1 | 4/2006 | Grinberg et al. |
| 2006/0095044 | A1 | 5/2006 | Grady, Jr. et al. |
| 2006/0149375 | A1 | 7/2006 | Yuan et al. |
| 2006/0241385 | A1 | 10/2006 | Dietz |
| 2007/0227216 | A1 | 10/2007 | Schalliol |
| 2007/0288030 | A1 | 12/2007 | Metzger et al. |
| 2008/0086127 | A1 | 4/2008 | Patterson et al. |
| 2008/0114370 | A1 * | 5/2008 | Schoenefeld ...... A61B 17/1721 606/96 |
| 2008/0161815 | A1 | 7/2008 | Schoenefeld et al. |
| 2008/0183214 | A1 | 7/2008 | Copp et al. |
| 2008/0255564 | A1 | 10/2008 | Michelson |
| 2008/0257363 | A1 | 10/2008 | Schoenefeld et al. |
| 2008/0275452 | A1 | 11/2008 | Lang et al. |
| 2008/0306552 | A1 | 12/2008 | Winslow |
| 2008/0312659 | A1 | 12/2008 | Metzger et al. |
| 2008/0319491 | A1 | 12/2008 | Schoenefeld |
| 2009/0076555 | A1 | 3/2009 | Lowry et al. |
| 2009/0087276 | A1 | 4/2009 | Rose |
| 2009/0088674 | A1 * | 4/2009 | Caillouette .......... A61B 5/4528 600/595 |
| 2009/0088761 | A1 * | 4/2009 | Roose .................. A61B 17/155 606/87 |
| 2009/0088763 | A1 * | 4/2009 | Aram .................. A61B 17/155 606/88 |
| 2009/0093816 | A1 * | 4/2009 | Roose ................ A61B 17/1764 128/898 |
| 2009/0099567 | A1 * | 4/2009 | Zajac .................. A61B 17/155 128/898 |
| 2009/0105760 | A1 | 4/2009 | Frey |
| 2009/0110498 | A1 | 4/2009 | Park |
| 2009/0138020 | A1 | 5/2009 | Park et al. |
| 2009/0187194 | A1 | 7/2009 | Hamada |
| 2009/0198277 | A1 | 8/2009 | Gordon et al. |
| 2009/0254093 | A1 | 10/2009 | White et al. |
| 2009/0270868 | A1 | 10/2009 | Park et al. |
| 2009/0326537 | A1 | 12/2009 | Anderson |
| 2010/0016984 | A1 | 1/2010 | Trabish |
| 2010/0049195 | A1 | 2/2010 | Park et al. |
| 2010/0082035 | A1 | 4/2010 | Keefer |
| 2010/0087829 | A1 | 4/2010 | Metzger et al. |
| 2010/0100193 | A1 | 4/2010 | White |
| 2010/0152782 | A1 | 6/2010 | Stone et al. |
| 2010/0185204 | A1 | 7/2010 | Buttermann et al. |
| 2010/0191244 | A1 | 7/2010 | White et al. |
| 2010/0217270 | A1 | 8/2010 | Polinski et al. |
| 2010/0217336 | A1 | 8/2010 | Crawford et al. |
| 2010/0305700 | A1 | 12/2010 | Ben-Arye et al. |
| 2010/0324692 | A1 | 12/2010 | Uthgenannt et al. |
| 2011/0015636 | A1 | 1/2011 | Katrana et al. |
| 2011/0015639 | A1 | 1/2011 | Metzger et al. |
| 2011/0046735 | A1 | 2/2011 | Metzger et al. |
| 2011/0054478 | A1 | 3/2011 | Vanasse et al. |
| 2011/0071533 | A1 | 3/2011 | Metzger et al. |
| 2011/0046628 | A1 | 4/2011 | Jamali |
| 2011/0093023 | A1 | 4/2011 | Lee et al. |
| 2011/0093086 | A1 | 4/2011 | Witt et al. |
| 2011/0160736 | A1 | 6/2011 | Meridew et al. |
| 2011/0160867 | A1 | 6/2011 | Meridew et al. |
| 2011/0166578 | A1 | 7/2011 | Stone et al. |
| 2011/0184419 | A1 | 7/2011 | Meridew et al. |
| 2011/0184526 | A1 | 7/2011 | White et al. |
| 2011/0190899 | A1 | 8/2011 | Pierce et al. |
| 2011/0213376 | A1 | 9/2011 | Maxson et al. |
| 2011/0218545 | A1 | 9/2011 | Catanzarite et al. |
| 2011/0224674 | A1 | 9/2011 | White et al. |
| 2011/0288433 | A1 | 11/2011 | Kelleher et al. |
| 2011/0319745 | A1 * | 12/2011 | Frey .................. A61B 17/15 600/407 |
| 2012/0041445 | A1 * | 2/2012 | Roose ................ A61B 17/1746 606/96 |
| 2012/0130434 | A1 | 5/2012 | Stemniski et al. |
| 2012/0150243 | A9 | 6/2012 | Crawford et al. |
| 2012/0179259 | A1 | 7/2012 | McDonough et al. |
| 2012/0215315 | A1 | 8/2012 | Hochscheul et al. |
| 2012/0245587 | A1 | 9/2012 | Fang |
| 2013/0006251 | A1 | 1/2013 | Aram et al. |
| 2013/0053854 | A1 | 2/2013 | Schoenefeld et al. |
| 2013/0110174 | A1 | 5/2013 | Marik |
| 2013/0123850 | A1 | 5/2013 | Schoenefeld et al. |
| 2013/0218163 | A1 | 8/2013 | Frey |
| 2014/0137618 | A1 | 5/2014 | Isaacs |
| 2014/0350614 | A1 | 11/2014 | Frey |
| 2014/0379032 | A1 | 12/2014 | Hennard |
| 2015/0047410 | A1 | 2/2015 | Petit et al. |
| 2015/0127053 | A1 | 5/2015 | Maruenda Paulino et al. |
| 2015/0297249 | A1 | 10/2015 | Catanzarite |
| 2016/0030067 | A1 | 2/2016 | Frey et al. |
| 2016/0270802 | A1 | 9/2016 | Fang et al. |
| 2017/0215857 | A1 | 8/2017 | D'Urso |
| 2017/0312032 | A1 * | 11/2017 | Amanatullah ........ G09B 23/30 |
| 2018/0082480 | A1 * | 3/2018 | White .................. G06T 11/00 |
| 2018/0168740 | A1 * | 6/2018 | Ryan .................. A61B 90/36 |

FOREIGN PATENT DOCUMENTS

| | | |
|---|---|---|
| CN | 201275138 | 7/2009 |
| CN | 201404283 | 2/2010 |
| CN | 101390773 | 11/2010 |
| CN | 101953713 | 1/2011 |
| CN | 104306061 | 1/2015 |
| CN | 105078563 | 11/2015 |
| CN | 106175911 | 12/2016 |
| CN | 104224306 | 8/2017 |
| DE | 102013110699 | 4/2015 |
| DE | 202014011170 U1 | 4/2018 |
| EP | 2168507 | 3/2010 |
| EP | 2957244 | 12/2015 |
| EP | 2749235 | 8/2017 |
| EP | 3381382 | 10/2018 |
| FR | 3012030 | 12/2015 |
| FR | 3023655 | 4/2018 |
| GB | 2447702 | 9/2008 |
| JP | 2006-528533 | 12/2006 |
| JP | 2008-514362 | 5/2008 |
| JP | 2012-143379 | 8/2012 |
| JP | D1508406 | 10/2014 |
| WO | WO2001037728 | 8/2002 |

(56) References Cited

FOREIGN PATENT DOCUMENTS

| | | |
|---|---|---|
| WO | WO2004071314 | 8/2004 |
| WO | WO2006039266 | 4/2006 |
| WO | WO2007145937 | 12/2007 |
| WO | WO2008027549 | 3/2008 |
| WO | WO2009004625 | 1/2009 |
| WO | WO2009035358 | 3/2009 |
| WO | WO2006017641 | 4/2009 |
| WO | WO2008157412 | 4/2009 |
| WO | WO2009129063 | 10/2009 |
| WO | WO2009105106 | 12/2009 |
| WO | WO2010033431 | 3/2010 |
| WO | WO2010148103 | 12/2010 |
| WO | WO2011041398 | 4/2011 |
| WO | WO2011080260 | 7/2011 |
| WO | WO2011106711 | 9/2011 |
| WO | WO2011109260 | 9/2011 |
| WO | WO2012082164 | 6/2012 |
| WO | WO2012152900 | 11/2012 |
| WO | WO2013041618 | 3/2013 |
| WO | WO2013104682 | 7/2013 |
| WO | WO2013169674 | 11/2013 |
| WO | WO2013173700 | 11/2013 |
| WO | WO2014070889 | 5/2014 |
| WO | WO2014088801 | 6/2014 |
| WO | WO2014090908 | 6/2014 |
| WO | WO2014095853 | 6/2014 |
| WO | WO2014143762 | 9/2014 |
| WO | WO2014198279 | 12/2014 |
| WO | WO2016148675 | 9/2016 |

OTHER PUBLICATIONS

Dai et al. "Surgical treatment of the osteoporotic spine with bone cement-injectable cannulated pedicle screw fixation: technical description and preliminary application in 43 patients," Clinics, Feb. 2015, vol. 70, No. 2, pp. 114-119.
Extended Search Report for European Patent Application No. 11804191.2, dated May 7, 2015. 8 pages.
Extended Search Report for European Patent Application No. 13778164.7, dated Feb. 17, 2016. 10 pages.
Hong et al. "Binder-jetting 3D printing and alloy development of new biodegradable Fe—Mn—Ca/Mg alloys," Acta Biomaterialia, Nov. 2016, vol. 45, pp. 375-386 (Abstract only) 4 pages.
International Preliminary Report on Patentability for International (PCT) Patent Application No. PCT/US11/42412 dated Jan. 17, 2013, 7 pages.
International Preliminary Report on Patentability for International Patent Application No. PCT/US2013/036535, dated Oct. 30, 2014, 7 pages.
International Preliminary Report on Patentability for International Patent Application No. PCT/US2014/041379, dated Dec. 17, 2015, 6 pages.
International Preliminary Report on Patentability for International Patent Application No. PCT/US2015/032356, dated Dec. 15, 2016, 7 pages.
International Search Report and Written Opinion for International Patent Application No. PCT/US11/42412, dated Nov. 8, 2011.
International Search Report and Written Opinion for International Patent Application No. PCT/US15/32356, dated Oct. 28, 2015, 10 pages.
International Search Report and Written Opinion for International Patent Application No. PCT/US2013/036535, dated Jun. 26, 2013, 8 pages.
International Search Report and Written Opinion for International Patent Application No. PCT/US2014/041379, dated Oct. 28, 2014, 7 pages.
International Search Report and Written Opinion for International Patent Application No. PCT/US2016/056970, dated Mar. 10, 2017, 13 pages.

Introducing IntelliSense Drill Technology®, McGinley Orthopaedic Innovations, 1 page, [captured Feb. 29, 2016 from: http://web.archive.org/web/20160229042028/http://www.mcginleyorthopaedicinnovations.com/index.php?/pages/drill].
Jakus et al. "Hyperelastic "bone": A highly versatile, growth factor-free, osteoregenerative, scalable, and surgically friendly biomaterial," Science Translational Medicine, Sep. 2016, vol. 8, No. 358, pp. 358ra127 (Abstract only) 5 pages.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).
Lu et al. "A Novel Patient-Specific Navigational Template for Cervical Pedicle Screw Placement," Spine, Dec. 15, 2009, vol. 34, No. 26, pp. E959-E966 (Abstract Only).
Notice of Allowance for U.S. Appl. No. 13/172,683 dated Apr. 23, 2014 ., 7 pages.
Notice of Allowance for U.S. Appl. No. 13/841,069, dated Sep. 18, 2014. 7 pages.
Notice of Allowance for U.S. Appl. No. 14/298,624, dated Oct. 7, 2015. 7 pages.
Notice of Allowance for U.S. Appl. No. 14/883,299, dated Mar. 20, 2017. 12 pages.
Notice of Allowance for U.S. Appl. No. 29/409,734, dated May 11, 2012. 8 pages.
Notice of Allowance for U.S. Appl. No. 29/427,918, dated Oct. 15, 2012. 9 pages.
Notice of Allowance for U.S. Appl. No. 29/432,668 dated Nov. 27, 2013. 11 pages.
Notice of Allowance for U.S. Appl. No. 29/476,699, dated Oct. 2, 2015. 8 pages.
Notice of Allowance for U.S. Appl. No. 29/476,705, dated Oct. 7, 2015. 8 pages.
Notice of Allowance for U.S. Appl. No. 29/476,709, dated Nov. 6, 2015. 8 pages.
Notice of Allowance for U.S. Appl. No. 29/496,231, dated Jul. 23, 2015. 10 pages.
Notice of Allowance for U.S. Appl. No. 29/538,633, dated Jan. 6, 2016. 10 pages.
Notice of Allowance with English Translation for Japan Patent Application No. 2013-518663, dated Dec. 8, 2015. 4 pages.
Notice off Allowance with English Translation for Japan Patent Application No. 2015-507078, dated Jan. 10, 2017. 4 pages.
Official Action for Australian Patent Application No. 2011276468 dated Apr. 10, 2013, 3 Pages.
Official Action for Canada Patent Application No. 2,802,094, dated Feb. 14, 2017, 4 pages.
Official Action for Canada Patent Application No. 2,914,005, dated Feb. 3, 2017, 3 pages.
Official Action for China Patent Application No. 201180029692.7, dated Oct. 8, 2014 12 pages.
Official Action for European Patent Application No. 11804191.2, dated Feb. 17, 2017, 5 pages.
Official Action for U.S. Appl. No. 13/172,683, dated Feb. 24, 2014, 10 pages.
Official Action for U.S. Appl. No. 13/172,683, dated Sep. 10, 2013 7 pages.
Official Action for U.S. Appl. No. 13/841,069, dated Jul. 8, 2014, 6 pages.
Official Action for U.S. Appl. No. 13/841,069, dated Jul. 31, 2014 9 pages.
Official Action for U.S. Appl. No. 14/298,634, dated Apr. 27, 2015 8 pages.
Official Action for U.S. Appl. No. 14/298,634, dated Jul. 7, 2015 6 pages.
Official Action with English Translation for China Patent Application No. 201380030638.3, dated Feb. 4, 2017. 6 pages.
Official Action with English Translation for China Patent Application No. 201380030638.3, dated May 25, 2016. 11 pages.
Official Action with English Translation for Japan Patent Application No. 2013-518663, dated May 12, 2015. 4 pages.
Official Action with English Translation for Russia Patent Application No. 2014143528/14, dated Jan. 13, 2017. 8 pages.

(56) References Cited

OTHER PUBLICATIONS

Owen et al. "Rapid prototype patient-specific drill template for cervical pedicle screw placement." Computer Aided Surgery, Sep. 2007, vol. 12, No. 5, pp. 303-308 (Abstract Only).
Partial Search Report for European Patent Application No. 11804191.2, dated Jan. 20, 2015 6 pages.
Ryken et al. "Image-based drill templates for cervical pedicle screw placement Laboratory investigation," Journal of Neurosurgery, Jan. 2009, vol. 10, No. 1 (Abstract Only).
Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).
Examination Report No. 1 for AU2016338436, dated Sep. 22, 2020. 6 pages.
Examiner Requisition for CA3001898, dated Jan. 7, 2020. 3 pages.
Examination Report for IN20182701734, dated Jun. 23, 2020. 6 pages.
Examination Report for IN201617045149, dated Jun. 12, 2020. 5 pages.
Office Action in BR112018007443-8, dated Jun. 9, 2020. 4 pages.
Translated Office Action from Japanese Patent Application No. 2018-519856, dated Oct. 6, 2020. 3 pages.

\* cited by examiner

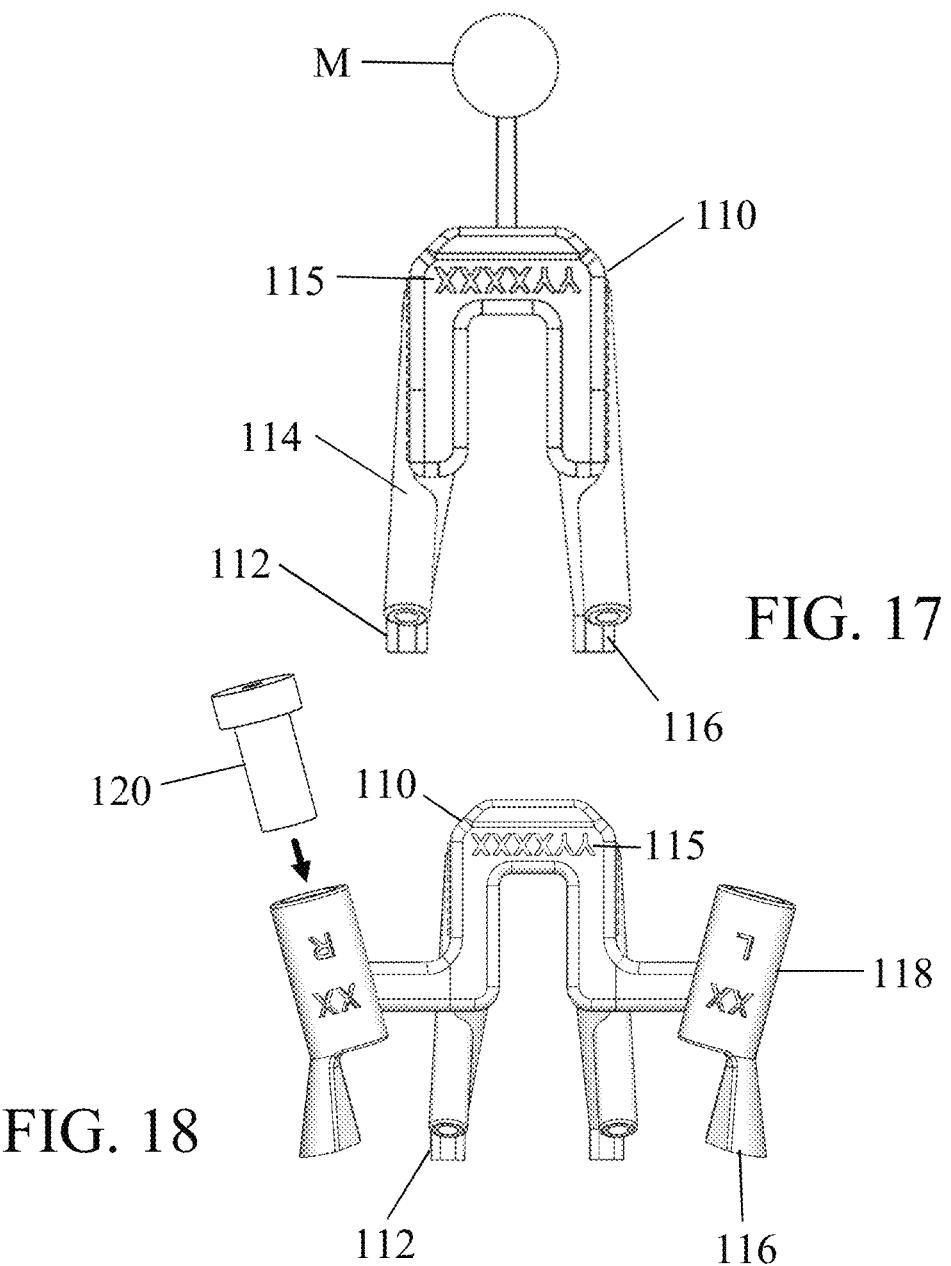

PATIENT-MATCHED APPARATUS FOR USE IN AUGMENTED REALITY ASSISTED SURGICAL PROCEDURES AND METHODS FOR USING THE SAME

CROSS REFERENCE TO RELATED APPLICATIONS

This application claims the benefit of U.S. Provisional Patent Application Ser. No. 62/823,911, filed Mar. 26, 2019, the entirety of which is incorporated herein by reference. This application is a continuation-in-part of U.S. patent application Ser. No. 16/598,861, filed on Oct. 10, 2019, which claims priority under 35 U.S.C. § 119(e) to U.S. Provisional Application Ser. No. 62/743,661, filed Oct. 10, 2018, and which is also a continuation-in-part of U.S. patent application Ser. No. 15/997,404, filed Jun. 4, 2018, which is a continuation-in-part of U.S. patent application Ser. No. 15/416,975, filed on Jan. 26, 2017, which issued as U.S. Pat. No. 9,987,024 on Jun. 5, 2018, which in turn is a continuation-in-part of U.S. patent application Ser. No. 14/883,299, filed Oct. 14, 2015, which issued as U.S. Pat. No. 9,642,633 on May 9, 2017, and claims priority under 35 U.S.C. § 119(e) to U.S. Provisional Patent Application 62/373,855, filed Aug. 11, 2016, to U.S. Provisional Patent Application Ser. No. 62/362,440, filed Jul. 14, 2016, and to U.S. Provisional Patent Application Ser. No. 62/287,134, filed Jan. 26, 2016. U.S. patent application Ser. No. 14/883,299 is a continuation-in-part of U.S. patent application Ser. No. 14/298,634, filed Jun. 6, 2014, which issued as U.S. Pat. No. 9,198,678 on Dec. 1, 2015, and claims priority under 35 U.S.C. § 119(e) to U.S. Provisional Application Ser. No. 62/162,466, filed May 15, 2015. U.S. Patent Application Ser. No. 14/298,634, claims the priority to U.S. Provisional Patent Application Ser. Nos. 61/877,837 filed Sep. 13, 2013, 61/845,463 filed Jul. 12, 2013, and 61/832,583 filed Jun. 7, 2013, and is a continuation-in-part of U.S. patent Application Ser. No. 13/841,069, filed Mar. 15, 2013, which issued as U.S. Pat. No. 8,870,889 on Oct. 28, 2014 and claims the priority to U.S. Provisional Patent Application Nos. 61/625,559 filed Apr. 17, 2012, 61/393,695 filed Oct. 15, 2010, and 61/359,710 filed Jun. 29, 2010. U.S. patent application Ser. No. 13/841,069 is a continuation in part of U.S. patent application Ser. No. 13/172,683, filed Jun. 29, 2011, which issued as U.S. Pat. No. 8,758,357 on Jun. 24, 2014. U.S. patent application Ser. No. 13/172,683 claims priority to U.S. Provisional Patent Application Nos. 61/393,695 filed Oct. 15, 2010, and 61/359,710 filed Jun. 29, 2010. U.S. patent application Ser. No. 15/997,404 also claims priority under 35 U.S.C. § 119(e) to U.S. Provisional Patent Application Ser. No. 62/628,626 filed Feb. 9, 2018. The entireties of these applications and patents are incorporated by reference herein.

FIELD OF THE INVENTION

The present disclosure generally relates to the field of medical devices, and more specifically toward systems for use with a patient-specific or patient-matched surgical device based on the patient's unique anatomical features. The present disclosure also relates to methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan that accounts for the unique and sometimes irregular anatomical features of a particular patient. For example, the implantation of orthopedic screws or other fixation devices in a patient's boney anatomy is well accepted amongst surgeons who treat various orthopedic pathologies. Although the performance of various screw constructs has become predictable, there are still multiple challenges with the placement and insertion of the orthopedic screws or other fixation devices. The challenges occur, for example, when a surgeon is unable to reference boney landmarks due to previous surgery or when the patient's anatomy is irregular in shape, or when a particular trajectory for insertion of the screws (or other fixation devices) is impeded by anatomical obstructions.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a customized surgical guide and/or implant based on the dynamic nature of the anatomical structures the customized guide/implant is designed to associate with. This data, while currently used by surgeons in surgery planning, is largely unused for creating a customized set of instruments or other surgical devices that are designed to complement the patient's unique anatomy.

In addition, virtual reality and/or augmented reality systems (collectively referred to as "AR" in this disclosure) have provided advantages to surgeons with respect to surgical planning and in particular the ability of surgeons to visual the orientation and placement of orthopedic implants and/or instruments. The surgeon would therefore benefit from the enhanced ability to merge AR capabilities with patient-specific surgical devices and/or equipment, as well as customized manufacturing and placement of patient-specific guides/implants. While various types of augmented reality (AR) systems are provided in the prior art, several are not applicable or usable with the current state of surgical equipment, including those AR systems that pertain to driving assistance for vehicles, games, and entertainment attractions. In addition, different localization methods may be used with prior art AR systems, such as sensor-based localization methods relying on the use of many sensors. As another example, certain AR systems rely on a global positioning system (GPS) sensor and/or an inertial measurement unit (IMU) sensor to verify a location and a direction of an object. When high accuracy is required, a sensor-based localization method requires a specific (and often expensive) sensor with a high degree of accuracy, but is not practical in surgical settings. Furthermore, many prior art vision-based localization methods rely on specific camera information to acquire highly precise information, yet are difficult to use in a surgical environment.

Specific surgical procedures are often performed in the spinal and/or cephalad region of a patient. The procedures performed in these areas are often designed to stop and/or eliminate all motion, including by removal and/or destruction of some or all of the boney anatomy in the patient's boney anatomy and/or implantable fixation devices (i.e., plates or screws) for limiting movement of the boney anatomy of the particular patient. By eliminating movement, pain and degenerative disease may be reduced or avoided.

A significant danger of performing operations on a patient's orthopedic anatomy, and in particular accessing an intervertebral space during a MIS surgery on the spine, is that of inadvertently contacting or damaging the para-spinal nerves, including the exiting nerve roots, traversing nerves and the nerves of the cauda equina. The exact location of these para-spinal nerves cannot be precisely determined prior to the commencement of surgery, and therefore are dependent on a surgeon's ability to visually locate the same after the initial incision is made. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannula are received through the patient's back, such as when performing minimally invasive spinal surgery, minor blood vessels are ruptured, thereby blocking the surgeon's vision inside the intervertebral region after the cannula has been inserted. Other anatomical features at a particular patient may also obstruct the surgeon's view or make it difficult to provide illumination within the cannula. Therefore, one particular shortcoming that is addressed by the present disclosure is to provide devices which are patient-matched to facilitate proper location and orientation without use of microscopes or other equipment and that otherwise eliminate the problems associated with prior art procedures on the spine, including MIS procedures.

As described herein, the prior art fails to teach a system for creating patient-specific or patient-matched surgical apparatus, based on the data set derived from the MRI or CT scan, for use with robotic and AR systems. The use of the patient-specific data set for a vertebral or other anatomic body of a particular patient may allow a surgeon to accommodate for subtle variations in the position and orientation of a screw, plate or other bone anchor to avoid particular boney anatomy or irregularities in the positioning and alignment of the adjoining vertebral bodies.

As another example, the use of these data sets may also assist a surgeon in selecting a desired trajectory for an implantable device so as to avoid sensitive anatomical features of a particular patient or to secure a bone anchoring device in a particular area of desired bone density during an actual procedure. The use of patient-specific data sets further permits the surgeon to avoid mistakes by creating customized tools and instruments, which may comprise orientation, end-stops or other safety related features to avoid over-torque and/or over-insertion of any implantable devices. The use of patient-specific data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide apparatus suitable for use with a surgical procedure and/or patient-specific apparatus that is adapted to conform to a plurality of anatomical features of a particular patient and that otherwise assists a surgeon in completing the surgical procedure(s) safely and efficiently. It is also advantageous to provide a procedure and/or apparatus that otherwise significantly reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel system and method is described for developing customized apparatus for use in one or more surgical procedures, particularly those procedures associated with the occipital bone of the cephalad. The systems and methods described herein incorporate a patient's unique morphology, which may be derived from capturing MRI, CT, or other data to derive one or more "Patient Matched" apparatus, which comprises complementary surfaces based on a plurality of data points from the MRI, CT or other anatomical data. Each "Patient Matched" apparatus is matched and oriented around the patient's own anatomy, and is preferably configured to incorporate specific and/or desired insertional trajectories (which may be verified in a pre-operative setting using 3D CAD software, such as the software disclosed in WO 2008027549, which is incorporated by reference herein in its entirety). According to one embodiment described herein, other apparatus used during the surgical procedure may facilitate the orientation and/or placement of one or more implants, including plates, screws, fixation devices, etc.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Various surgical procedures using the apparatus and systems described herein may be performed with sequential or simultaneous introduction of rods, pins, plates, screws or other surgical devices into adjacent boney anatomy to join various portions of, for example, an occipital bone and/or cervical vertebrae (particularly C1-C2) of a particular patient. Such procedures often require introduction of additional tools to prepare a site for implantation. These tools may include drills, drill guides, debridement tools, irrigation devices, vises, clamps, cannula, and other insertion/retraction tools.

Orthopedic and other surgeries may be performed by a number of different procedures, as opposed to conventional surgical procedures and methods, which typically require cutting of muscles, removal of bone, and retraction of other natural elements. During a MIS procedure, for example, including procedures using the apparatus of the present invention, a less destructive approach to the patient anatomy is carried out by using retractor tubes or portals, which take advantage of anatomy and current technology to limit the damage to intervening structures.

In typical surgical procedures, skeletal landmarks are established fluoroscopically and a small incision is made over the landmark(s). According to various methods known in the prior art, a series of dilators may be applied until one or more cannula is placed over the anatomic structure. In some procedures, a microscope is then placed over the operative site to provide illumination and magnification with a three-dimensional view of the anatomical site to ensure that the surgeon is able to accurately locate the desired patient anatomy and properly position and orient any tool, instrument or other surgical device used during the procedure. The microscope, however, is an expensive and unwieldy device requiring uncomfortable gyrations of the surgeon's back and neck in order to gain the necessary view and is a nuisance to drape (a large, sterile plastic bag has to be placed over the eight-foot-tall structure). The use of adequate illumination is also difficult to direct due to the size of the microscope.

The customized and integrated matching aspects of this presently disclosed system provides an advantage over the prior art, in particular by providing a plurality of interlocking and/or matching points for each apparatus, which are easily or efficiently registerable and positionable using robotic and AR systems, which in turn reduces the likelihood of misalignment, misplacement and subsequent mistake during the surgical procedure(s).

Accordingly, one aspect of the present disclosure is to provide a method for preparing a customized surgical device or instrument, which in a preferred embodiment comprises, but is not limited to: (1) obtaining data associated with a patient's anatomy; (2) converting the data obtained to a 3-dimensional data set(s); (3) determining at least one trajectory or path for facilitating a surgical procedure to be performed on the patient; (4) determining at least one surface associated with the patient's anatomy; (5) generating a 3-dimensional representation of the customized surgical device or instrument, which incorporates the at least one trajectory of path and a matching surface to the at least one surface associated with the patient's anatomy; (6) fabricating the customized surgical device or instrument using the 3-dimensional representation; (7) registering at least one marker on the customized surgical device with a robotic or an AR system; and (8) positioning the customized surgical device on the patient's anatomy utilizing the at least one surface associated with the patient's anatomy and the at least one marker.

According to this aspect described above, the method steps may further comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc.

According to yet another aspect of the present disclosure, the system and method includes use of data obtained from a radiographic imaging machine, an ultrasonic machine, a bone density scanning machine, or a nuclear medicine scanning device.

In another aspect, the patient-matching features may be confirmed by one or more additional process, such as fluoroscopy or other processes known to those of skill in the art.

In one aspect of the present disclosure, the method comprises the use of bone density data obtained through a CT scan of the patient anatomy for use in planning the trajectory of a surgical guide and corresponding fixation device or instrument, such as a cutting/routing/drilling instrument intended to penetrate the boney anatomy. This data may be used in other manners contemplated and described herein to assist the surgeon in planning, visualizing or otherwise preparing for the surgical procedure for the patient.

In yet another alternative embodiment, the data obtained from one of the scanning devices described above may be supplemented or merged with data from a bone density scanner to fabricate a device that is designed to remain in the patient after the surgical procedure is completed. It is to be expressly understood that data from a bone density scanner is not necessary to practice the inventions described herein, but may supplement the data and assist a surgeon or other medical professional in determining the proper location, trajectory, orientation or alignment of the various apparatus described herein.

According to yet another aspect of the present disclosure, data may be supplemented or merged with data from a bone density scanner to achieve further control over the orientation of any desired axes, particularly where the surgical procedure involves insertion of one or more implantable devices.

According to yet another embodiment, the data obtained from the patient permits the apparatus to be manufactured with defined pathways through the apparatus, which are operatively associated with at least one tool, instrument, or implant, and which permit the at least one tool, instrument or implant to be inserted in the defined pathways in a consistent and reproducible manner. Examples of devices that are implanted or remain in the patient include anchoring devices such as screws, pins, clips, hooks, etc., and implantable devices such as spacers, replacement joints, replacement systems, cages, etc. The apparatus may comprise one or more stops located within the pathways for preventing a tool, instrument or implant from advancing beyond a predetermined distance.

In embodiments, the apparatus is a surgical guide that is oriented in at least one trajectory. The trajectory may be one of: (1) a cortical bone trajectory; (2) a pedicle screw trajectory; (3) a cortical trajectory; (4) a sacral pedicle trajectory; (5) a sacral alar trajectory; (6) an S2-alar-iliac trajectory; (7) an iliac trajectory; (8) a transarticular trajectory; (9) a lateral mass trajectory; (10) a translaminar trajectory; (11) a transcondylar trajectory; and (12) an occipital trajectory (for example, during an operation on a patient's occipital or surrounding cervical anatomy).

One aspect of the present disclosure is a patient-specific guide designed to fit on the occipital bone of the cephalad. According to this embodiment, the occipital guide is designed to be placed in a mating configuration on the occipital bone to provide location, trajectory, and depth of pilot holes for subsequent alignment/placement of an occipital plate. In certain alternate embodiments, the guide may be used to both align and "carry" the plate. Alternatively, the patient-specific guide may be removable once the plate or other implant is adequately positioned on the patient's boney anatomy.

In embodiments, patient-specific guides described herein may be used with various orientation or registration markers for identification by a robot. Certain guides may comprise an embedded chip, circuit or equivalent with presurgical planning information, which may be read by a machine and deliver specific instructions to a robotic surgical device, for example. Such patient-specific guides may be used on multiple levels of a patient's spine that are impacted by a particular surgical procedure, and thereby provide markers for registration and orientation without having to rescan the patient throughout the surgery. The robotic device may view the patient and position of the patient's unique anatomy through the identification of the markers, and thereby more rapidly align instrumentation controlled by the robotic equipment.

In embodiments, the patient-specific guides described herein comprises a locating feature for a robot or other autonomous device to align the guide to a vertebra in space, for example. With multiple locating guides placed on a patient's vertebra, a robot can drill into the vertebra, affix an orientation tool, and/or orient vertebra relative to each other to meet pre-surgically planned spinal alignment. Pre-surgically planned spinal alignment may also be matched to one or more pre-bent rods, minimizing surgical time. In other embodiments, the robot or other autonomous device may be configured to perform an osteotomy with known locations of vertebra relative to each other.

In embodiments, the surgical devices described herein may be used with an AR system or associated simulation device. In one embodiment, the AR capabilities are provided in conjunction with a physical guide, while in other embodiments the capabilities are provided in conjunction with a "virtual" guide. In one embodiment, the surgical device is configured as a patient-specific pedicle screw placement guide is for use with a surgical instrument or implantable device. The pedicle screw placement guide is preferably adapted to guide intra-operative placement of pedicle screws that are used to anchor a pedicle screw spinal system onto target portion of a patient's anatomy. In one embodiment, the target portion of the patient's anatomy is a posterior element of the patient's spine, including lumbar, interbody and cervical portions of a patient's spine.

One aspect of the present disclosure relates to a customized apparatus for use with an augmented reality system, comprising: a central portion of the apparatus, which comprises a first and a second extension; at least a first surface configured to be complementary to a predetermined portion of an anatomical feature; at least a second surface distinct from the at least a first surface that is configured to be complementary to another predetermined portion of an anatomical feature; at least one marker in communication with the augmented reality system; wherein the at least one marker communicates the location and orientation of the apparatus to the augmented reality system; and wherein placement of the at least a first surface on the predetermined portion of an anatomic feature and placement of the at least a second surface on the another predetermined portion of an anatomical feature is verified by the augmented reality system through communication with the at least one marker.

Another aspect of the present disclosure relates to a system for performing one or more surgical procedures facilitated by a computer-aided navigational apparatus, comprising: at least one robotic apparatus; a processor in communication with the at least one robotic apparatus; a patient-specific apparatus configured to be placed on at least one patient-specific feature; at least one marker that is positioned in a known location relative to patient anatomy and configured to transmit positional information to the processor; wherein the processor is configured to receive and relay the positional information received from the at least one marker to determine the location and orientation of the at least one robotic apparatus relative to patient anatomy.

In another embodiment, the pedicle screw placement guide utilizes anatomic landmarks that are identified pre-operatively by a medical imaging scan of the patient, as well as markers that are registerable using a robotic or AR system. Optionally, the medical imaging scan of the patient may include one or more of: an MRI scan, a CT scan, and an x-ray scan. Data obtained from the medical imaging scan may be used to generate a pre-operative plan for the patient and facilitate the operation for the specific patient. The pedicle screw placement guide is configured to be used in a surgical procedure to place a pedicle screw in a pre-operatively determined orientation or trajectory.

According to yet another aspect of the present disclosure, a preconfigured surgical template is disclosed, which comprises one or more guides for receiving at least one plate, such as an occipital plate. According to this embodiment, the template further comprise patient-contacting surfaces formed to be substantially congruent with the anatomical features of a patient. The preconfigured surgical template is configured such that the patient-contacting surfaces are configured to contact the plurality of anatomical features in a mating engagement, to ensure proper alignment and mounting of the guide or template, and the guides of the preconfigured surgical template are preferably oriented in a direction selected prior to manufacturing of the preconfigured surgical template to achieve desired positioning, aligning or advancing of a tool within the one or more guides.

According to yet another aspect of the present disclosure, a method for creating a template for use in a surgical operation is disclosed. The method includes, but is not limited to: (1) collecting data from the patient corresponding to the patient's unique anatomy; (2) creating a model of the template from the data collected, the model comprising a plurality of matching surfaces to the patient's unique anatomy; (3) providing data associated with model to fabrication machinery; (4) rapidly generating the template to comprise the plurality of matching surfaces and further comprising at least one additional matching surface corresponding to at least one tool or instrument used in the surgical operation; and (5) generating a permanent device based on the template for use in the surgical operation.

In one embodiment of the present disclosure, the model is a digital model. In another embodiment of the present disclosure, the model is a physical model.

It is another aspect of the present disclosure to provide a patient-specific guide for use in a surgical procedure. The guide includes, but is not limited to: (1) a medial body having a proximal portion and a distal portion; (2) at least one cannula comprising a proximal and distal portion and a bore oriented in a direction determined from the anatomical features of a patient, the bore adapted to guide an instrument or a fixation device in a desired trajectory; and (3) a surface of the guide including patient-specific contours determined from the patient's anatomy and configured to contact and substantially conform to at least a first subcutaneous anatomic feature of the patient.

In certain embodiments, the guide further comprises one or more surfaces configured to avoid potentially damaging contact between the surfaces of the guide and surrounding tissue. In one embodiment, the surface in substantially planar and acts a shield to soft tissue on the opposite side of the spinous process as the at least one cannula. In embodiments, the shielding surface of the guide may be removable or adjustable to account for specific tissue the surgeon or health professional preferences.

In one embodiment, the bore of the at least one cannula may have different diameters and/or trajectories between one guide and another. In one embodiment, the bore is directed in a first predetermined trajectory. In another embodiment, the bore(s) are directed in a first and a second predetermined trajectory. In another embodiment, the bore(s) are directed in a plurality of trajectories, each different from the others.

In still another embodiment, the body further comprises a second bore that is oriented in a direction for placement of a fixation device. The guide may further comprise a second surface including patient-specific contours determined from the patient's anatomy and configured to contact and substantially conform to a second anatomic feature of the patient. Additionally, the medial body may optionally include at least one extension from the medial body, the at least extension including a second surface including patient-specific contours determined from the patient's anatomy and configured to contact and substantially conform to a second anatomic feature of the patient.

In one embodiment, at least one surface of the apparatus, such as the surface with the patient-specific contours, is adapted to hook at least partially around a specific portion of the patient's anatomy. In another embodiment, at least a portion of the guide is shaped to prevent contact with a portion of the patient's anatomy.

In still another embodiment, the medial body of the guide comprises a first portion releasably interconnected to a second portion. Optionally, the body may comprise at least two portions. In one embodiment, the portions of the body are adapted to be interconnected together.

In one embodiment, at least a portion of one of the extensions is adapted to hook at least partially around, and substantially conform to, a second anatomic feature of the patient. In one embodiment, at least one of the extensions is adapted to contact a portion of the patient's anatomy that has been altered by a surgical procedure. In another embodiment, at least one of the extensions is adapted to contact an unaltered portion of the patient's anatomy.

The guides and models described herein may comprise one or more of a polymeric material and a metallic material. In another embodiments, the model and/or guide includes at least one patient-matched surface that is substantially congruent to a mating surface of a portion of the patient's anatomy. In one element, the mating surface is the occipital bone of the patient's cephalad.

Additionally, or alternatively, the guide sleeve and the instrument may comprise a conductive material such that the surgical guide may be subject to an electrical current for providing intra-operative monitoring (IOM) of the instrument during contact with the surgical guide and with the patient anatomy.

The surgical device may be used in one or more of a minimally invasive surgical procedure and a minimal access procedure. In one embodiment, the surgical device is configured for use in conjunction with a device that employs automated or semi-automated manipulation such that placement of the surgical device with respect to the anatomical feature may be performed remotely by an operator through a computer controller. In another embodiment, the surgical device is identifiable by optical, electronic, or radiological recognition means such that the location and orientation of the surgical device with respect to the anatomical feature is verifiable. In still another embodiment, the surgical device is configured for use in conjunction with a navigation device such that placement of the surgical device with respect to the anatomical feature assists with one or more of registration, stability, and motion tracking by the navigation device.

Incorporated by reference in their entireties are the following U.S. patents and patent applications and international publications directed generally to methods and apparatus related to surgical procedures, thus providing written description support for various aspects of the present disclosure. The U.S. patents and pending applications incorporated by reference are as follows: U.S. Pat. Nos. 9,295,497, 8,758,357, 8,419,740, 8,357,111, 8,298,237, 8,277,461, 8,257,083, 8,214,014, 8,206,396, 8,167,884, 8,159,753, 7,957,824, 7,844,356, 7,658,610, 7,623,902, 7,491,180, 7,235,076, 6,755,839, 6,711,432, 5,201,734, and 3,151,392, U.S. Design Pat. Nos. D705,929, D669,176, D672,038, D618,796, D606,195, D533,664, D532,515, D428,989, D420,132, D412,032, D403,066, and D359,557, and U.S. Pat. Pub. Nos. 2013/0123850, 2013/0053854, 2013/0218163, 2012/0215315, 2012/0179259, 2012/0130434, 2012/0041445, 2011/0319745, 2011/0288433, 2011/0224674, 2011/0218545, 2011/0213376, 2011/0190899, 2011/0184526, 2011/0184419, 2011/0166578, 2011/0160867, 2011/0160736, 2011/0093086, 2011/0093023, 2011/0071533, 2011/0054478, 2011/0046735, 2011/0015639, 2011/0015636, 2010/0324692, 2010/0305700, 2010/0217336, 2010/0217270, 2010/0191244, 2010/0152782, 2010/0100193, 2010/0087829, 2010/0082035, 2010/0049195, 2010/0016984, 2009/0270868, 2009/0254093, 2009/0198277, 2009/0187194, 2009/0138020, 2009/0110498, 2009/0099567, 2009/0093816, 2009/0088763, 2009/0088761, 2009/0088674, 2009/0087276, 2008/0319491, 2008/0312659, 2008/0275452, 2008/0257363, 2008/0183214, 2008/0161815, 2008/0114370, 2007/0288030, 2006/039266, 2006/0241385, 2006/0149375, 2006/0095044, 2006/0084986, 2005/0148843, 2004/0243481, and 2004/0097925. The international publications incorporated by reference are as follows: European Publication No. EP 2168507, and World Intellectual Property Organization Pub. Nos. WO 2013/104682, WO 2013/041618, WO 2012/152900, WO 2011/109260, WO 2011/106711, WO 2011/080260, WO 2011/041398, WO 2010/148103, WO 2010/033431, WO 2009/129063, WO 2008/027549, and WO 2007/145937, and Chinese Publication Nos. CN 201275138, CN 201404283, CN 101390773, and CN 101953713.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures. It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein. In the drawings:

FIG. 17 is an elevation view of another guide and marker according to embodiments of the present disclosure;

FIG. 18 is an elevation view of another guide and marker according to embodiments of the present disclosure;

DETAILED DESCRIPTION

Figure 1:
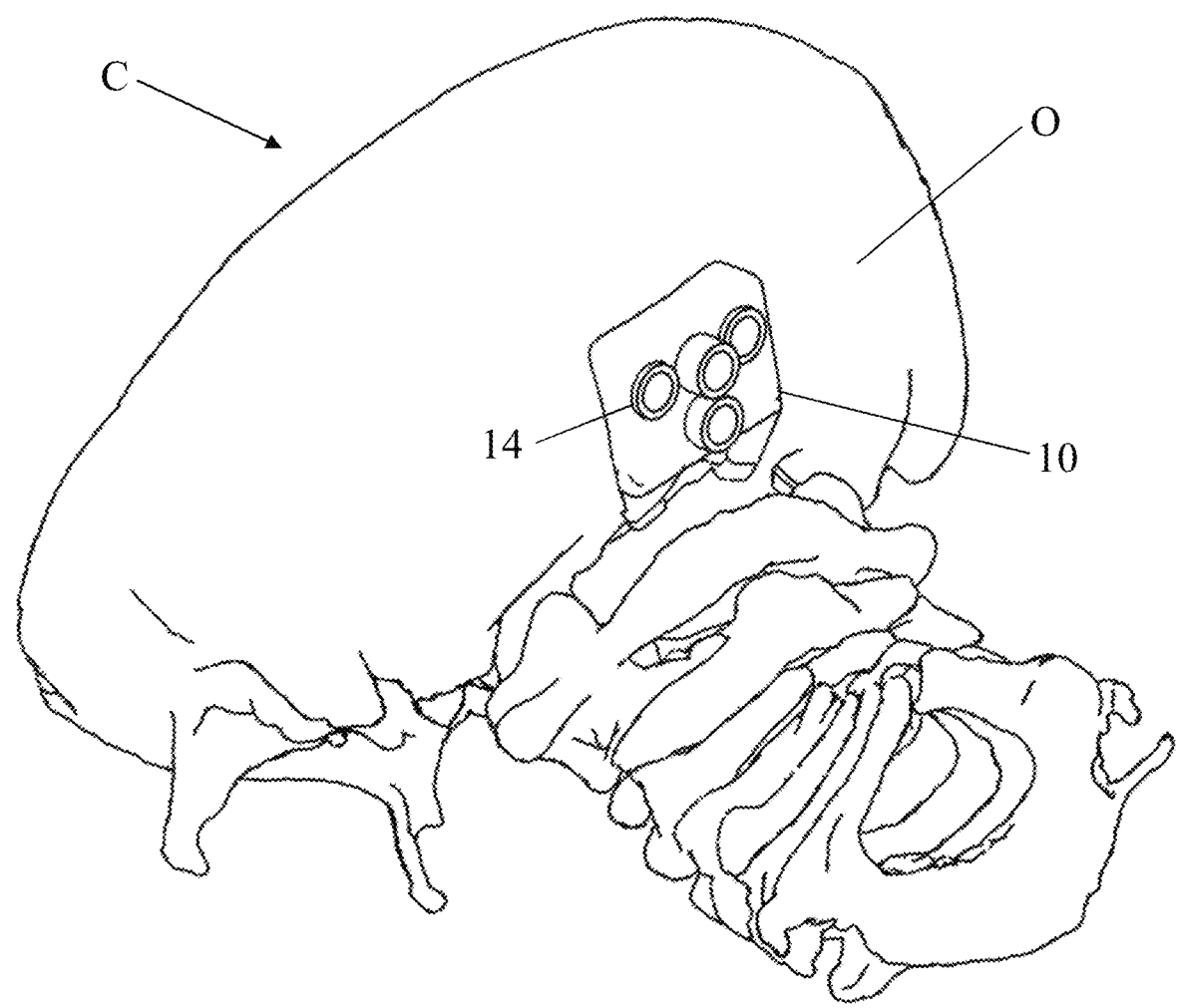
FIG. 1 is a perspective view of a patient-specific occipital guide according to embodiments of the present disclosure.

As shown in FIGS. 1-20B and described in further detail herein, the present disclosure relates to a novel system and method for design and use of a customized, patient-matched apparatus for use in a diverse number of surgical procedures, particularly those procedures involving robotic, computer-aided or other programmable equipment, or involving virtual or augmented reality systems. The apparatus preferably uses a patient's unique morphology, which may be derived from capturing MRI data, CT data, or any other medical imaging device to derive one or more patient-matched elements or components, which comprise complementary surfaces to those encountered during the surgical procedure(s) as derived from a set of data points. The apparatus may further comprise unique indicia, markers or equivalent for registration with the types of autonomous or augmented equipment described above.

According to various embodiments described herein, the patient-matched apparatus may further comprise desired axes and/or insertional trajectories. According to embodiments, the patient-matched apparatus may be further matched with at least other apparatus used during the surgical procedure. The apparatus may be configured to receive markers or may include markers embedded within the guide, the position of which (relative to the patient-contacting and other elements/components of the guide) are easily registered and determined by the autonomous or augmented equipment employed during the procedure. Other features of the disclosure will become apparent after a review of the following disclosures and varying embodiments of the disclosure.

Multiple embodiments of a guide according to certain aspects of the certain disclosure are depicted in FIGS. 1-20B. In embodiments, the apparatus is referred to as a surgical guide and is adapted to fit directly to aspects of a patient's anatomy. Referring to FIGS. 1-12D, the guide 10 may be positioned on an occipital bone O of the cephalad C. In preferred embodiments, the guide 10 is placed proximate to the foramen magnum. This "occipital" surgical guide 10 may comprise at least one lower patient-contacting surface 12 that permits the guide 10 to mate with one or more contours of a specific patient's occipital bone O. The guide 10 may comprise a plurality of pathways, referred to herein as cannula(e) 14, which preferably comprise bores therethrough for aligning or inserting one or more instruments or devices. Fixation devices, implants or instruments may be inserted through one or more of the cannula 14. In certain embodiments, one or more of the cannula 14, have distinct outer diameters, heights, bore diameters, etc. to distinguish one particular fixation device, implant or instrument insertional depth and orientation from other cannulae 14. In embodiments, the cannulae 14 are oriented and/or positioned in a specific location for placement of specific and/or patient-matched fixation or other devices. The cannulae 14 of a particular guide 10 may have different coloring, diameters, heights, etc. to visually distinguish one from the other during surgery, and may comprise unique indicia to further aid in this distinction. The bores in the cannula 10 may be depth specific to avoid under- of over-insertion of a particular device therethrough The guide 10 preferably provides a surgeon with means to ensure proper location, trajectory, and depth of pilot holes through the occipital bone O, such as for alignment and/or placement of an occipital plate and associated fixation devices (i.e., screws). The patient specific surface can be specific to any portion of the patient's anatomy, as reflected in the captured patient data using any of the various methods described above in the Summary.

Figure 2:
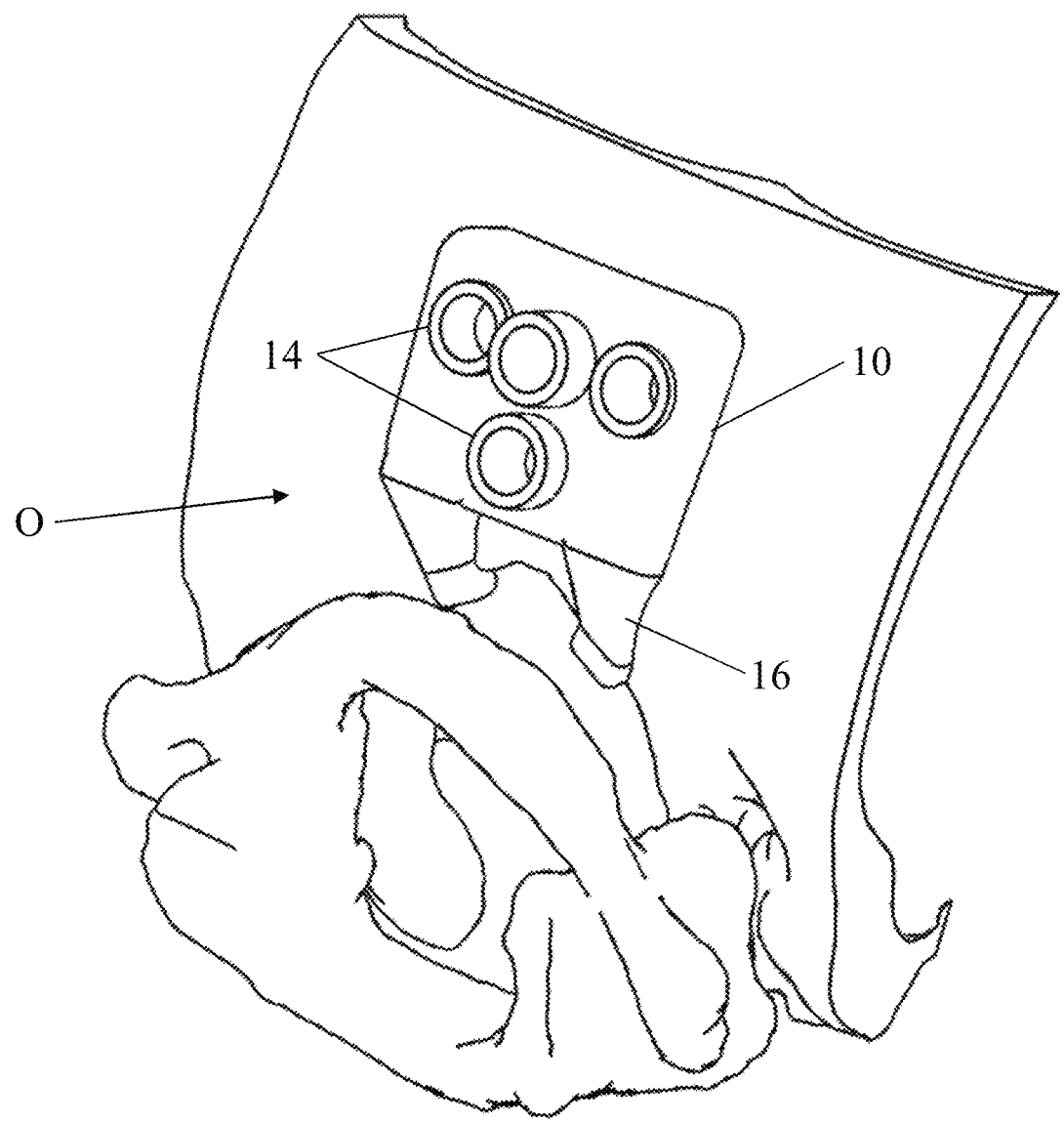
FIG. 2 is a perspective view of the patient-specific occipital guide shown in FIG. 1.
Figure 3:
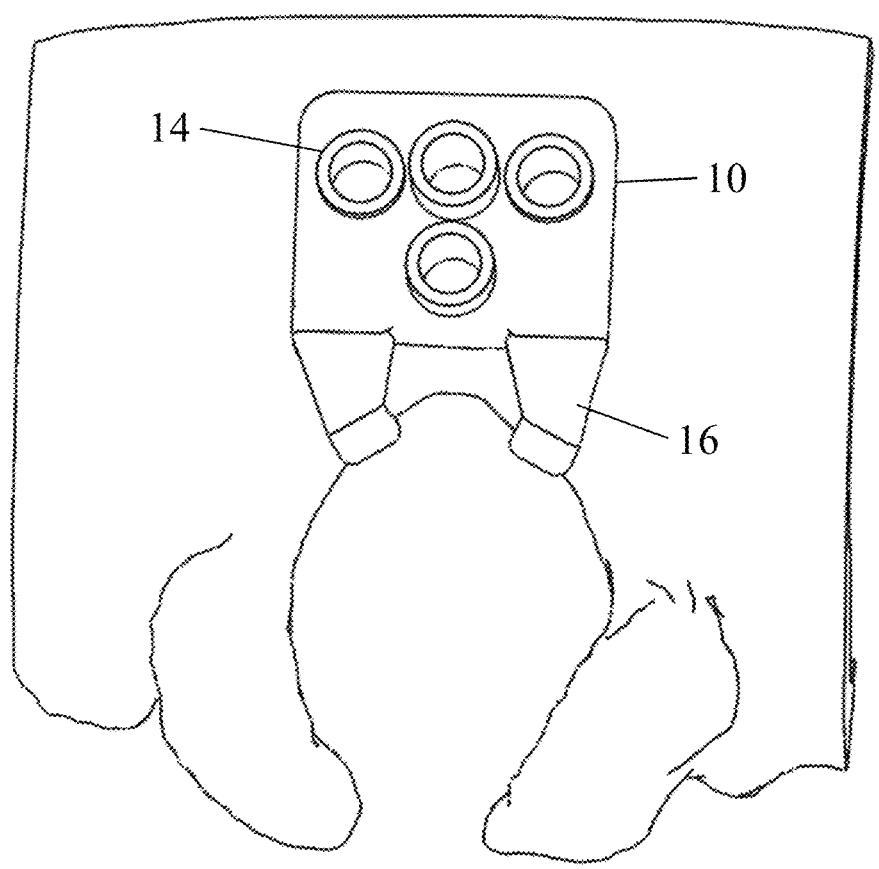
FIG. 3 is an elevation view of the patient-specific occipital guide shown in FIG. 1.

As illustrated in FIGS. 1-3, the occipital guide 10 according to one embodiment may comprise one or more extensions 16. Extensions 16 may be sized such that the body of the occipital guide 10 is appropriately located in the location of, for example, an occipital plate, and such that the distal ends of the extensions 16 terminate at the foramen magnum. In one embodiment, one or more extensions 16 may be sized, shaped or otherwise adapted to at least partially hook around a portion of the patient's foramen magnum to ensure proper placement and avoid movement of the guide 10 relative to the occipital bone. For example, the distal ends of the one or more extensions 16 may comprise shaped "hooks" that at least partially wrap around the foramen magnum and latch onto complementary surfaces of the specific patient. In certain embodiments, the extensions 16 or portions thereof may be at least semi-malleable so that the extensions 16 may deflect slightly and snap into place once engaged with the patient's foramen magnum. In other embodiments, the curvature or "hooks" of the extensions 16 may comprise compound curvatures, or otherwise have curves in at least two different planes formed by two distinct portions of the patient's anatomy.

Figure 4A:
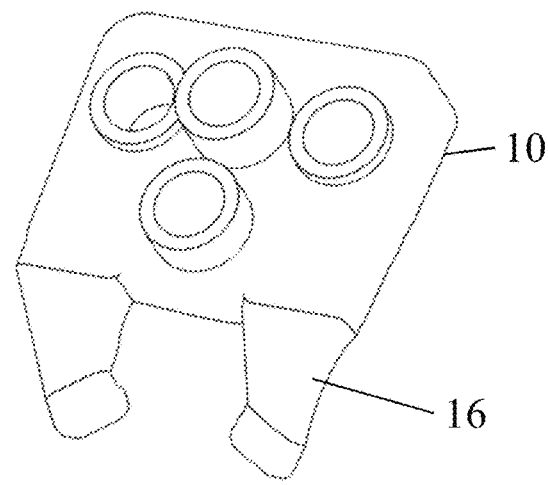
FIGS. 4A-4C are various perspective views of the guide shown in FIG. 1.
Figure 4B:
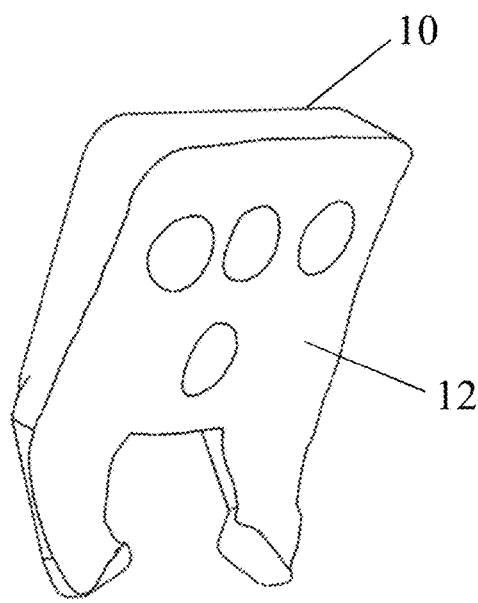
Figure 4C:
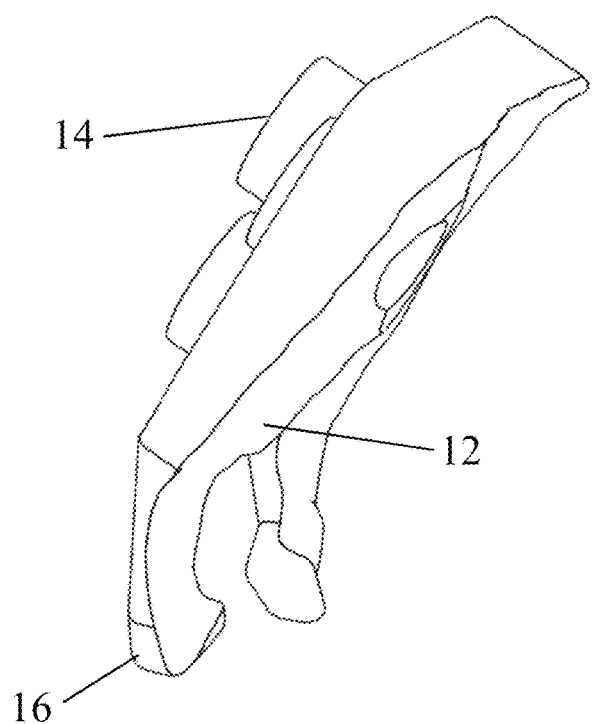

A single guide 10 may comprise multiple patient-specific surfaces, including on the body of the guide 10 and the one or more extensions (as best shown in FIG. 4C), such that a matching or mating connection is achieved about more than one portion of the patient's anatomy. Thus, the guide 10 may mate with specific portions of the patient's anatomy substantially simultaneously. In other embodiments, multiple guides 10 may be connected together, or portions of the occipital guide 10 may be removable and selectively reattached for specific procedures. For example, a particular guide 10 may be comprised of multiple parts that are selectively interconnectable to form the single guide, and thereby permit use of the guide 10 in a minimally invasive surgical procedure.

Referring to FIGS. 4A-4C, several perspective views of an occipital guide 10 according to embodiments is shown. Here, the guide 10 comprises at least one patient-matching surface 12 on a first side of the guide 10, which is adapted to substantially conform or mate with the occipital bone O of a particular patient. The opposite side of the guide 10 may comprise a plurality of cannulae 14 arranged in a predetermined location relative to the body of the guide 10, and preferably comprise bores therethrough for aligning or inserting one or more instruments or devices. For instance, fixation devices may be inserted through one or more of the cannula 14. In certain embodiments, one or more of the cannula 14 may be placed relative to an occipital plate (not shown). The bores in the cannula 10 may be depth specific to avoid under- of over-insertion of a particular device therethrough, as best shown in FIGS. 4A-4C. The guide 10 may comprise one or more extensions 16 as described above, which may mate with and or latch to the foramen magnum as shown best in FIGS. 2-3.

Figure 5A:
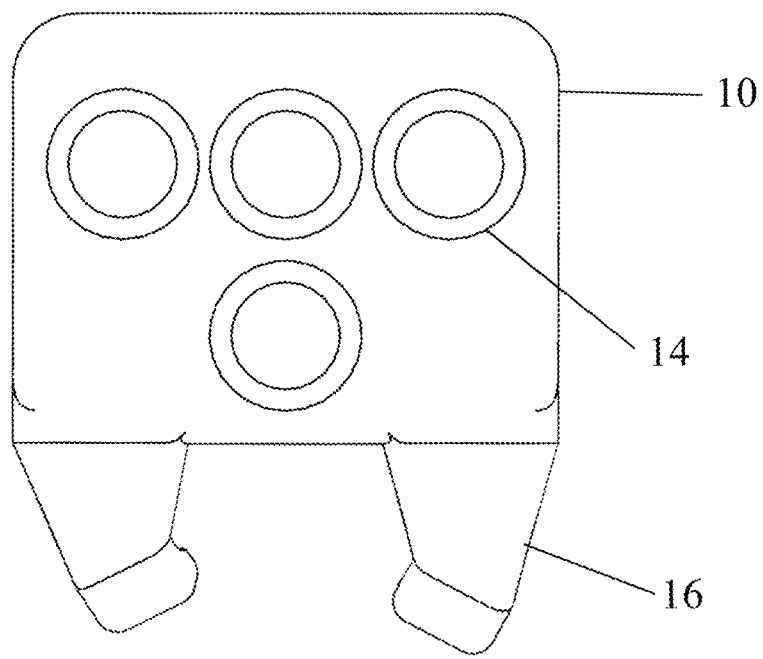
FIGS. 5A-5B are elevation views of an occipital guide according to alternate embodiments of the present disclosure.
Figure 5B:
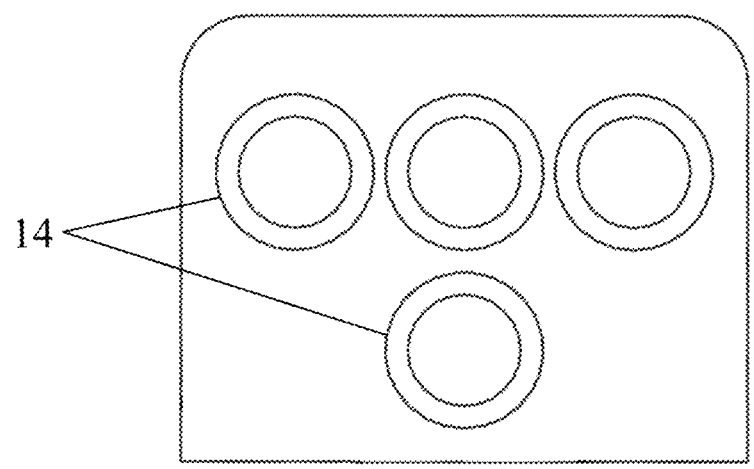

Referring now in particular to FIGS. 5A-5B, another embodiment is shown. In this embodiment, the guide 10 is preferably composed of multiple portions and/or multiple materials. The medial body of the guide 10 may be an implantable material, while the extensions 16 are removable from the medial body and comprised of a different material. In this version of the guide 10, the extensions 16 may be used to properly orient the guide 10 for drilling and after the holes have been drilled, the extensions 16 can be removed from the guide 10 so that only the medial body remains. In this manner, the guide 10 may be considered an implantable device, akin to a plate, and may be made of any known materials for implantation in a patient. For example, the medial body of the guide 10 may be comprised of titanium.

Figure 6:
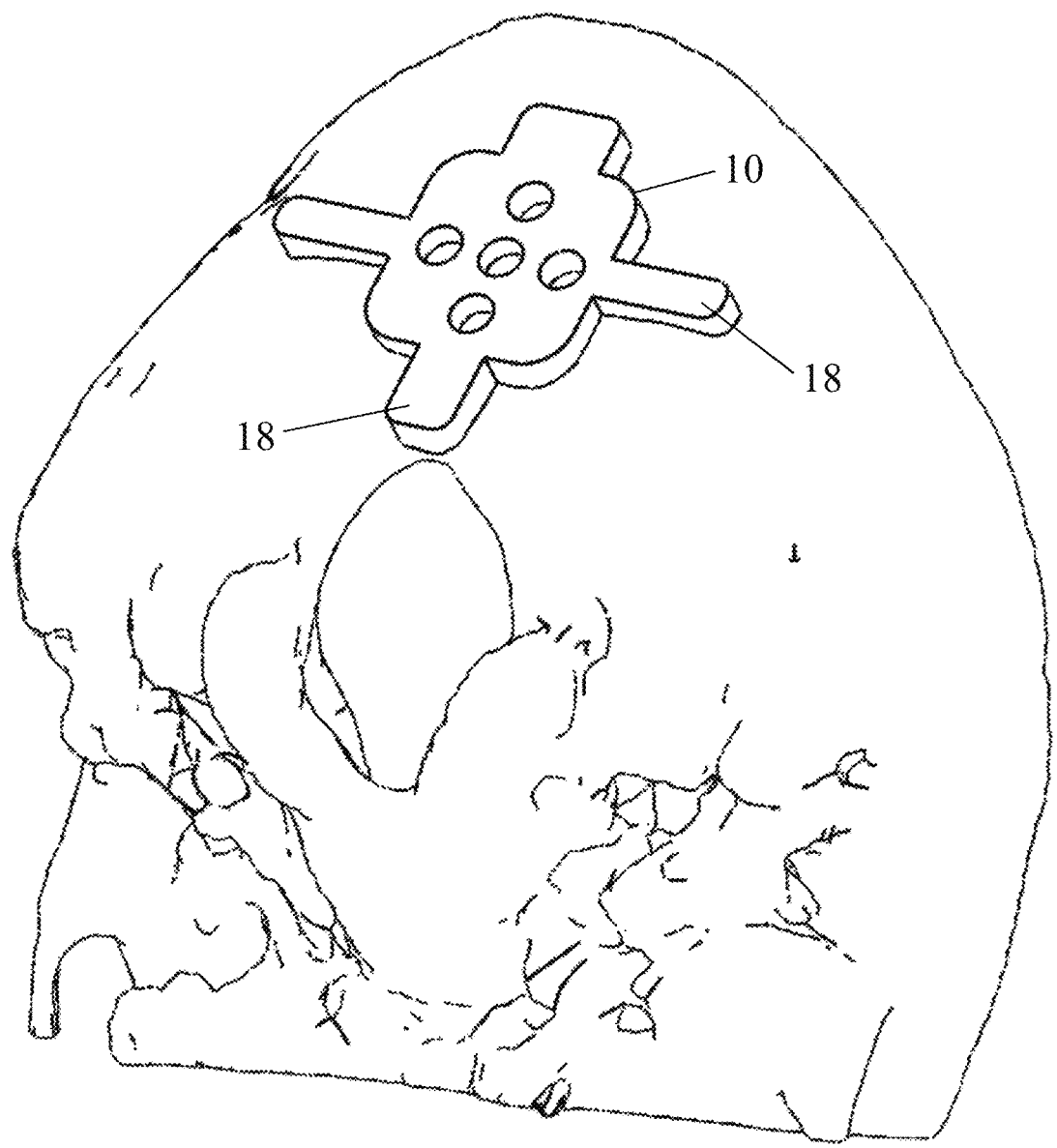
FIG. 6 is a perspective view of another guide according to embodiments of the present disclosure.
Figure 7:
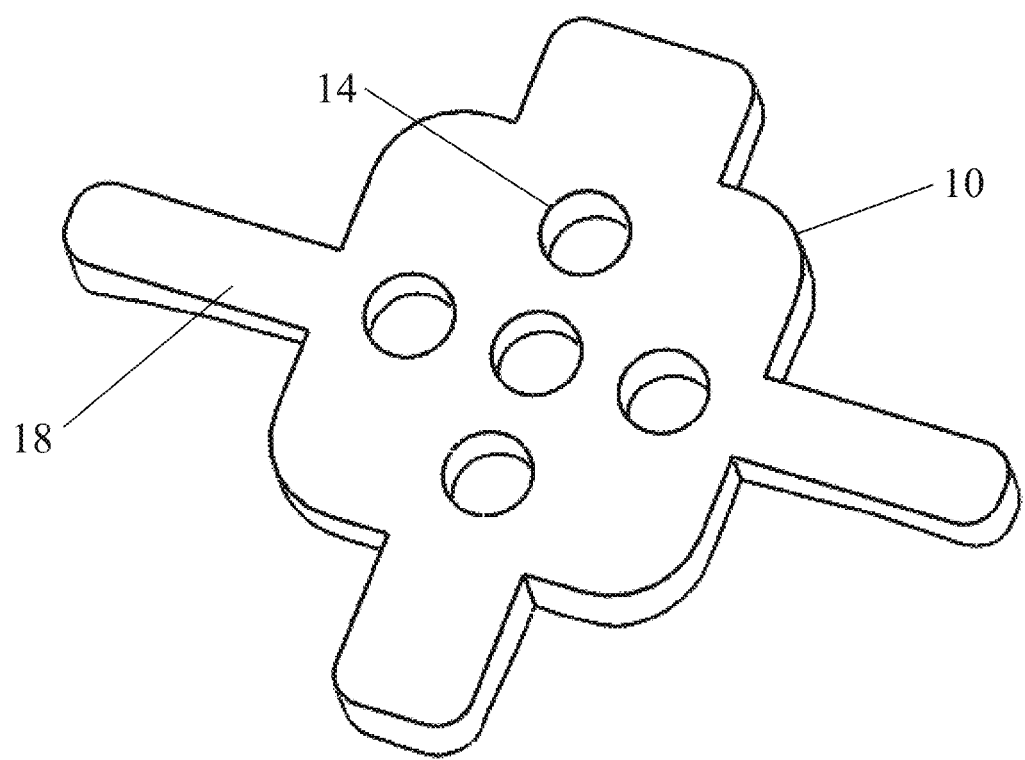
FIG. 7 is another perspective view of the guide shown in FIG. 6.
Figure 8:
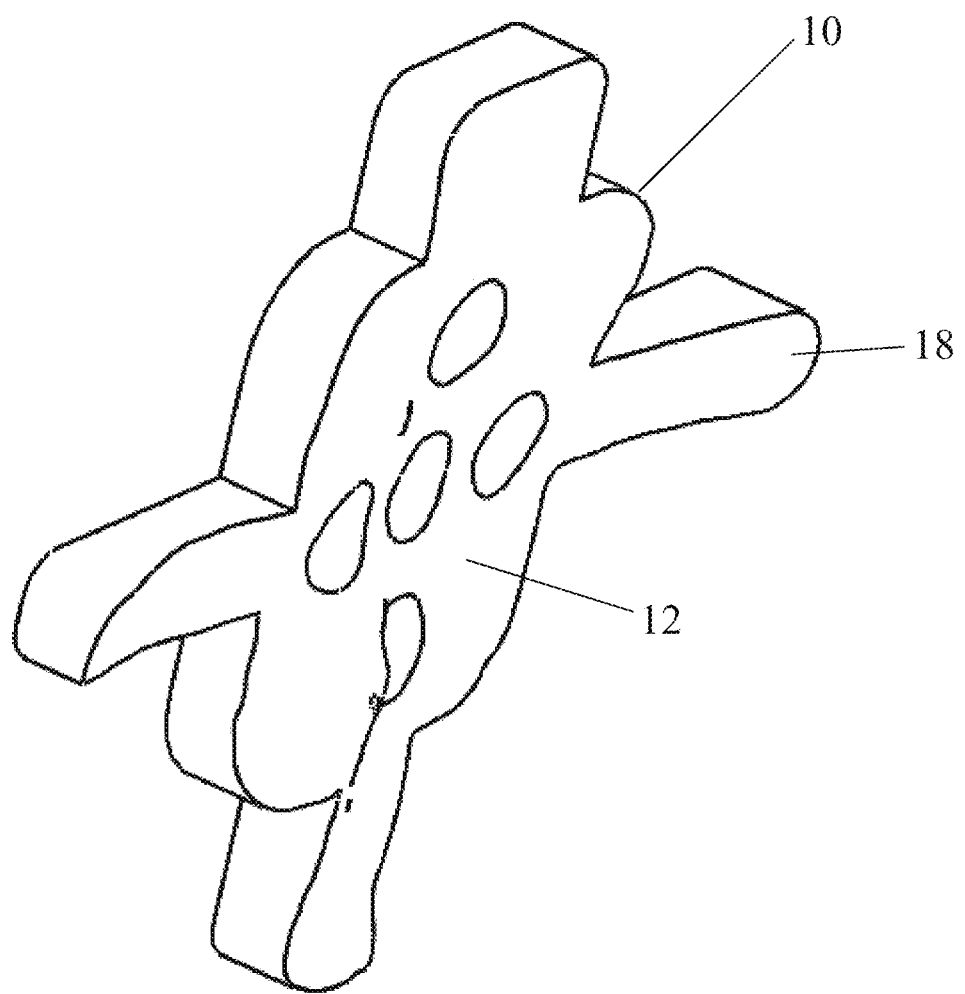
FIG. 8 is yet another perspective view of the guide shown in FIG. 6.

In yet other embodiments, and referring to FIGS. 6-8, the guide 10 may avoid contact with the foramen magnum. In this embodiment, the guide 10 may comprise various elongations 18 which stretch outwards from the body of the guide 10, in part to provide contact over a larger and/or more variable region of the patient's boney anatomy (e.g., external occipital protuberance, Nuchal lines, etc.) to ensure an adequate match between the patient-specific surface of the guide 10 and the complementary patient surface(s). Although exemplary guides 10 are shown in FIGS. 6-8, the elongations 18 may vary in number, length, and width from what is depicted in the figures.

Figure 9:
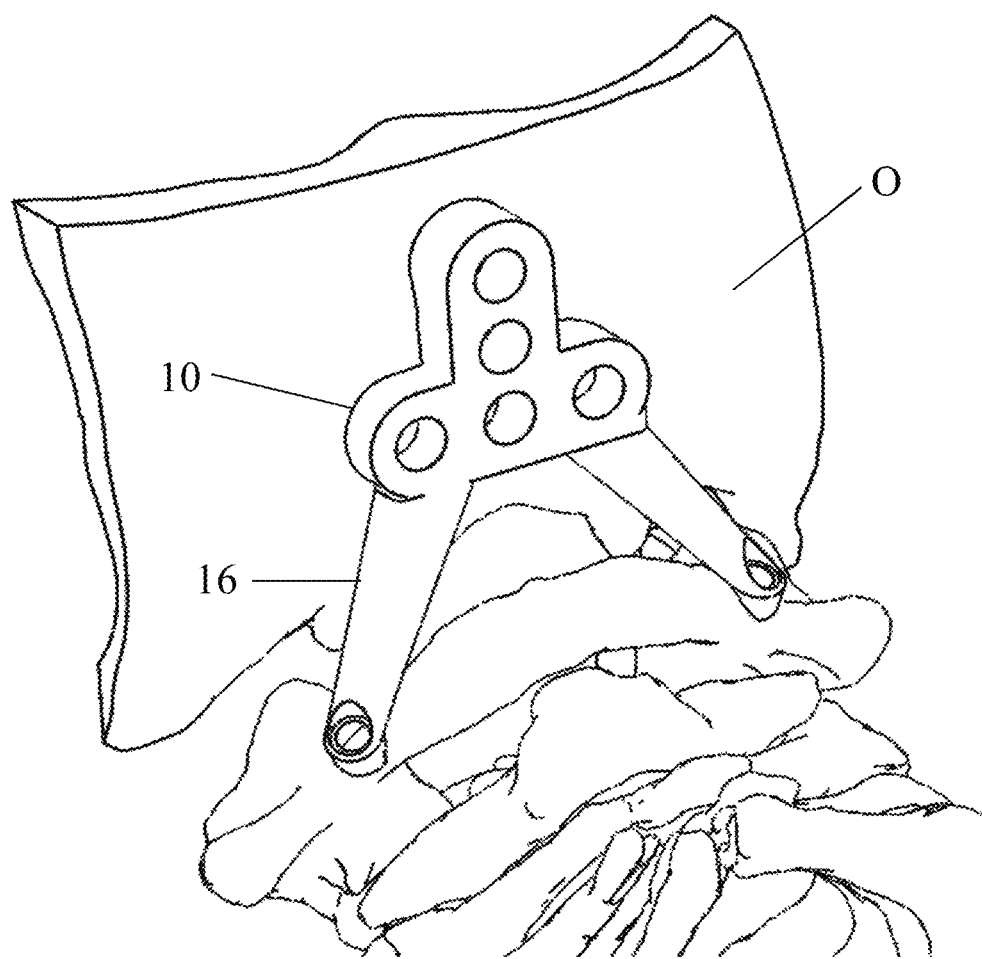
FIG. 9 is a perspective view of another guide according to embodiments of the present disclosure.

Referring now to FIG. 9, another embodiment of an occipital guide 10 is shown having one or more extensions 16 to a different patient anatomical feature. According to this embodiment, the guide 10 may contact the occipital bone O while further comprising extensions 16 connecting to any level of a patient's vertebrae. The extensions 16 may further comprise holes at the distal ends of the extensions 16. These holes may permit pilot holes to be drilled individually into the underlying boney anatomy, either before placing a plate or during placement of a plate (such as by employing the nesting guide described above). Alternatively, a plate with extensions may be fixed to the occiput first. The cervical vertebral level to be attached with the plate is preferably aligned with the extensions 16, and screw inserted through the hole(s) in the extensions 16 and through the plate. The occiput/plate/cervical level may thus be attached using posterior plate and screw fixation.

In this embodiment, the plate and extensions are preferably patient-matched and may be preplanned by design to drive location of preferred location of cervical vertebra relative to the patient's skull, occiput, and/or other cervical vertebra. By tightening a screw or other fixation device through the plate into cervical level, the extensions will align the level into correct contact location with the plate.

Still referring to FIG. 9, the guide 10 may contain additional extensions or connectors, which in certain embodiments are removeable from the body of the guide, and which may contact the C1 vertebra (or any other cervical level) to ensure proper orientation and/or stability of the guide. In the version of the guide 10 where a portion is implantable, the implantable portion may extend to C1 or C2 and provide trajectories for placing screws in those levels of the vertebrae as well. In this scenario, this device is acting not only as a guide, but also aligns anatomy with a specific amount of correction and maintains that correction, similar to a rod/screw construct. In other embodiments, the guide 10 may comprise a connector between C1 and C2, such that the guide and connector(s) span from Oct. to C2.

Figure 10:
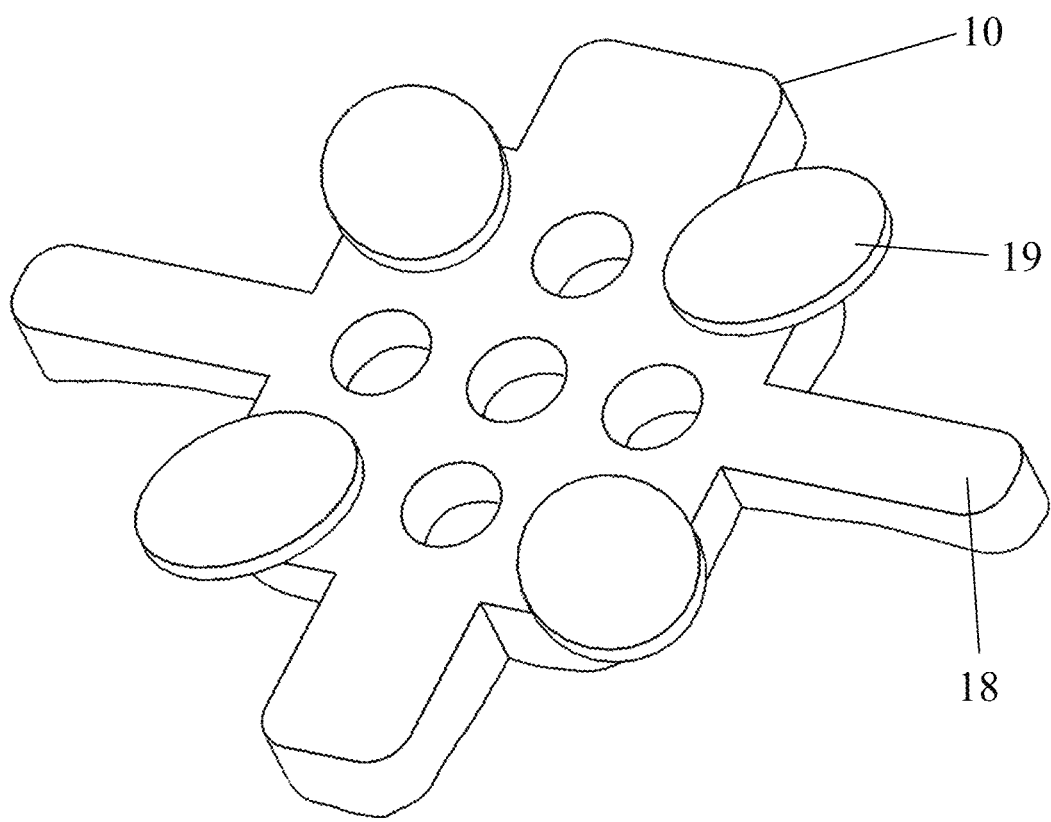
FIG. 10 is a perspective view of another guide according to embodiments of the present disclosure.
Figure 11A:
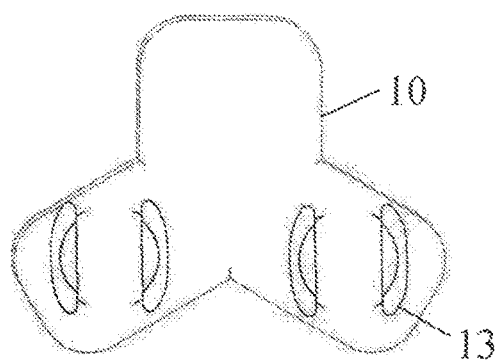
FIGS. 11A-E are various views of another guide according to embodiments of the present disclosure.
Figure 11B:
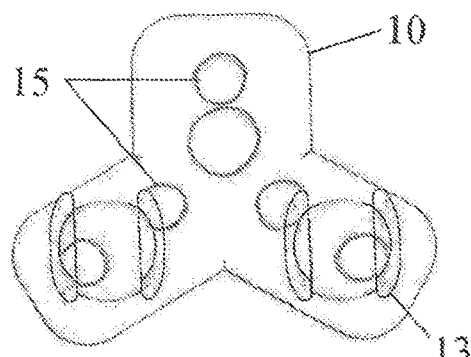
Figure 11C:
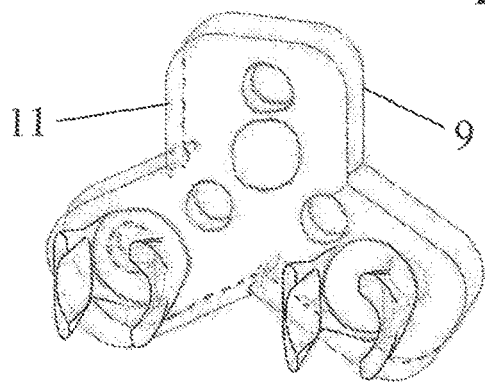
Figure 11D:
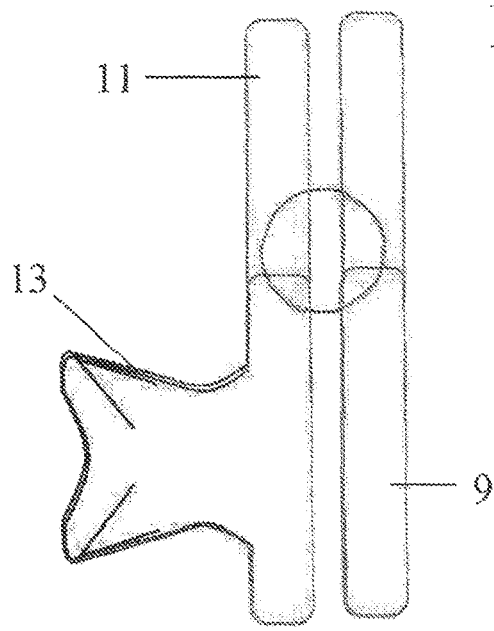
Figure 11E:
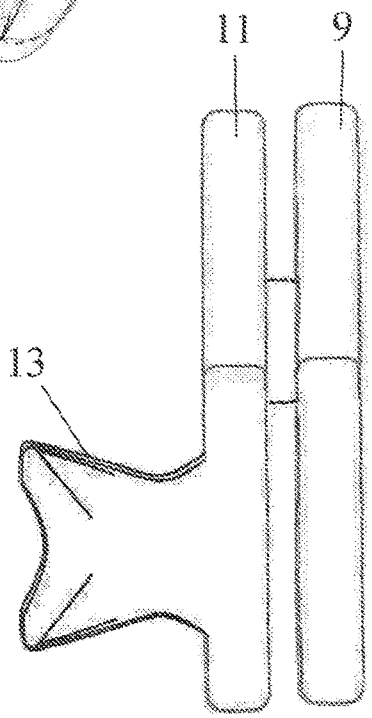
Figure 12A:
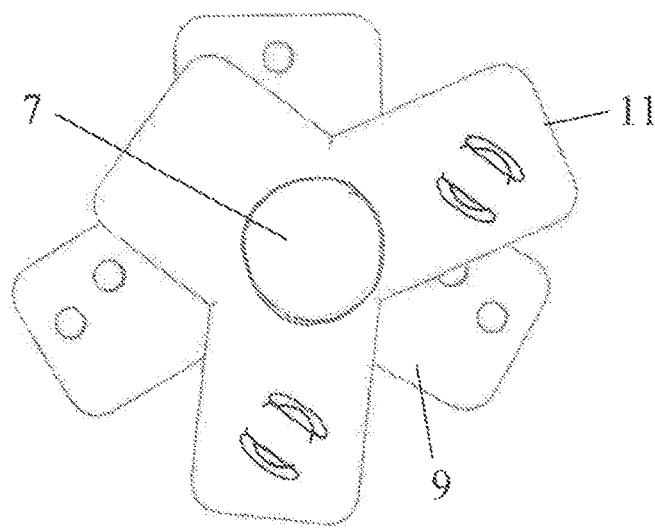
FIGS. 12A-D are additional views of the guide according to the embodiments of FIGS. 11A-E.
Figure 12B:
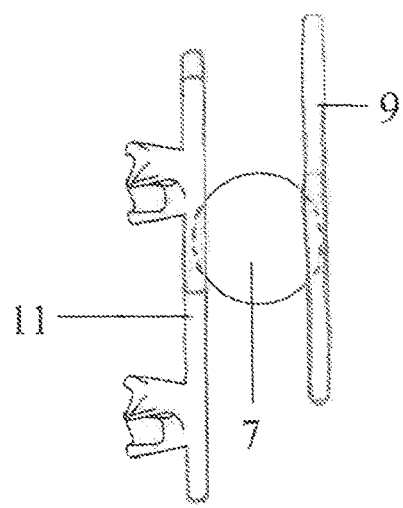
Figure 12C:
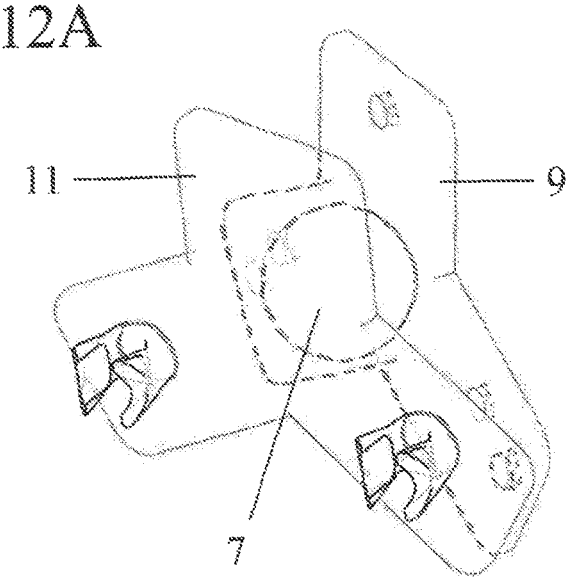
Figure 12D:
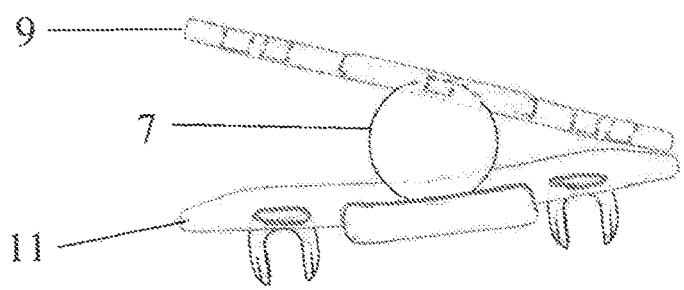

Referring to FIG. 10, the guide 10 may not include a large patient-specific surface as described above. Instead, the guide 10 may be held in place by fixation pins, suction, or by manual pressure applied to the body of the guide 10. The guide 10 may contain additional feature(s), referred to as pads 19, extending from the body that acts as a "pressure plate" where the user applies force to hold the guide in position. In certain embodiments, the pads 19 are patient-specific. In other embodiments, the pads 19 are not patient-specific.

The guide 10 may comprise an additional feature or surface oriented to identify, separate and/or protect critical anatomy such as the venous sinus. In one embodiment, the feature is comprised of a substantially planar surface of the guide 10 that acts a shield to soft or sensitive tissue. In other embodiments, the surface comprises an arcuate or curved surface to better distract the surrounding tissue while avoiding damage to the same. In embodiments, the shielding surface of the guide 10 may be removable or adjustable to account for specific tissue the surgeon or health professional preferences.

Referring now to FIGS. 11-A-E, another embodiment is shown. The guides 10 shown in these figures may utilize a patient-matched "dual" plate, wherein the rear plate 11 may be positioned either directly or with feet (either removable or permanent) that contact the foramen magnum (or other contact locations). The front plate 9 and the rear plate 11 may be moveable or positionable relative to one another, such as by rotating the front plate 9 or rear plate 11. The front and/or rear plate 9, 11 may comprise one or more apertures 15 for placement of one or more "tulips" 13 that can be placed through the apertures 15 as desired, and which extend from the surface of the rear plate 11 and/or front plate 9.

Once positioned, the front plate 9 may be moved out of the way to access the apertures 15 of the rear plate 11 or attached at a later time. Once screws or other fixation devices are in place, the front plate 9 may be attached or aligned with rods below the plate 9. The connection point 7 affixing the two plates may be constructed of various materials and may be various geometries. The front plate 9 preferably comprises tulips 13 that allow for affixing the occiput to the remainder of the fusion construct. Instead of tulips 13, a rod may come directly from the front plate 9, or the plate may contain holes to receive a rod construct. Once in place, the dual plates 9, 11 are able to move relative to one another allowing for the patient to remain mobile. Additionally, the locations for where the rods are attached to the front plate 9 may be able to move as well.

Figure 13A:
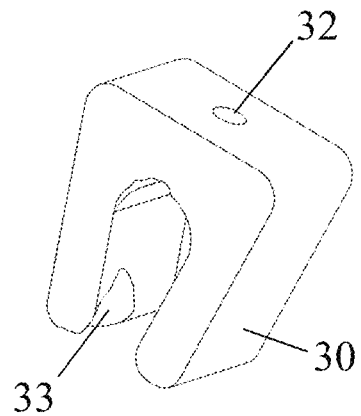
FIGS. 13A-C are various views of another guide according to embodiments of the present disclosure.

Referring to FIGS. 13A through 14C, a patient-specific apparatus 30 may be provided that attaches to various locations of a patient's anatomy. Referring first to FIGS. 13A-C, the patient-specific apparatus 30 preferably comprises at least three distinct surfaces 33, although in certain embodiments may comprise two or even one distinct surface, which are patient-specific or patient-matching (as best shown in FIG. 13B). These patient-specific surfaces 33 are designed to contact the patient in independent, unique locations, such as on a single vertebral level as shown in FIG. 13C.

As shown in FIG. 13A, the patient-specific apparatus 30 comprises a bore 32 with a pre-surgically planned orientation for creating a hole or opening in the underlying patient anatomy. The diameter, orientation, and depth of the hole is preferably be constrained by the bore 32 of the patient-specific apparatus 30, such as by a tapering bore 32 or a hard stop located at a set position within the bore 32 that prevents overtravel of a drill bit, for example. Once a tool is placed into the bore 32 and a hole has been created in the boney anatomy, the apparatus 30 may be removed.

Figure 14A:
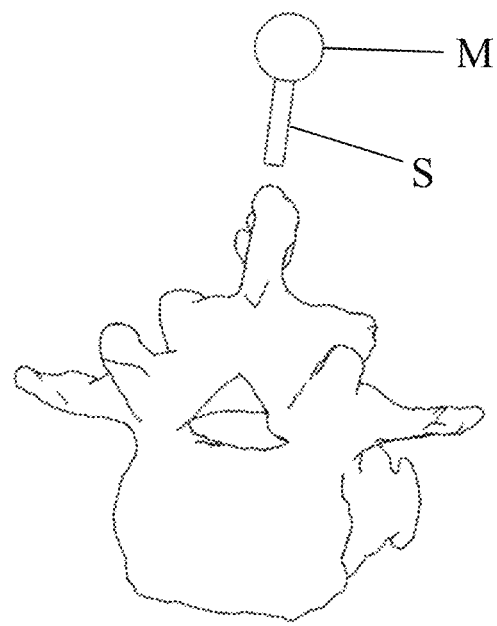
FIGS. 14A-C are perspective views of a marker placed using the guide according to the embodiments of FIGS. 13A-C.
Figure 14B:
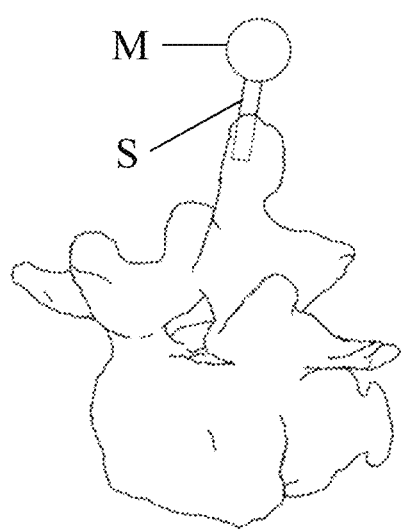
Figure 14C:
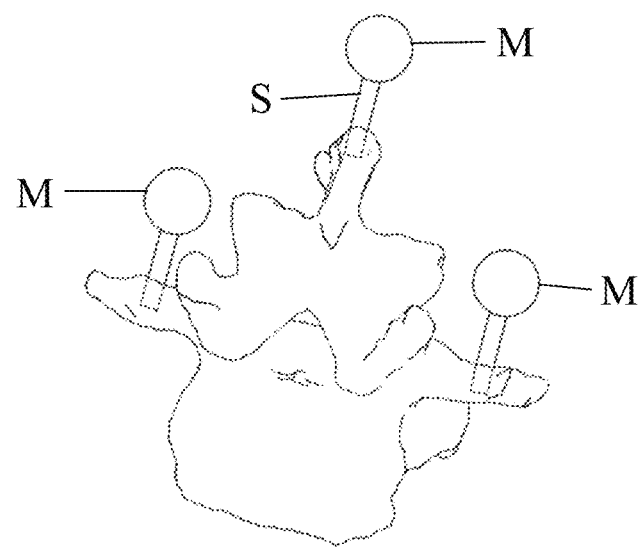

Referring now to FIGS. 14A-C, and preferably after removal of the apparatus 30, a registration marker M comprising a stem S sized to match the hole (such as with an interference or friction fit) is placed in the hole by inserting the stem S portion therein, as best shown in FIG. 14B. This process may be repeated using multiple registration markers M until sufficient markers have been embedded in the underlying anatomy for their position to be analyzed, as shown in FIG. 14C. By pre-surgically planning the location for the registration marker(s) M relative to patient-specific anatomy, robot-assisted navigation is able to mark the location of the boney anatomy via the marker(s) M and calibrate, regardless of intersegmental motion, through analysis of the orientation of registration markers M.

Figure 13B:
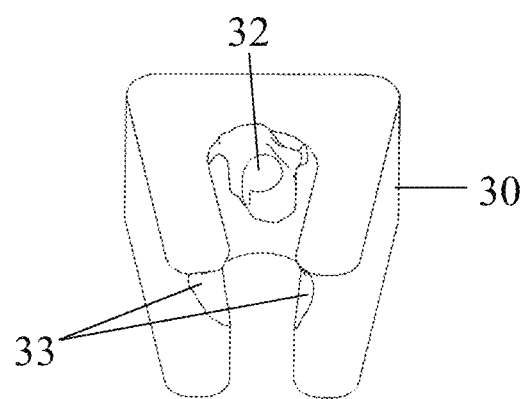
Figure 13C:
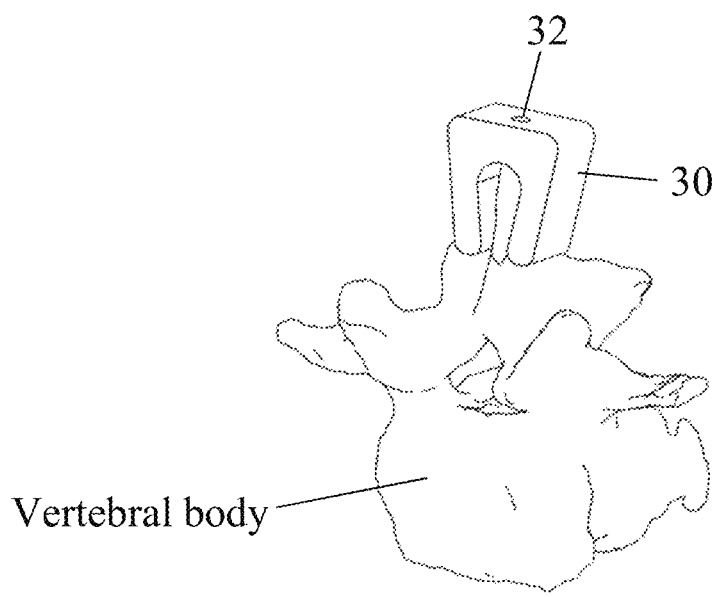

The apparatus 30 of FIGS. 13A-C may be positioned proximate to a medial vertebra, for example, including between superior and inferior vertebrae. Thus, the apparatus 30 may also comprise at least one lower patient-contacting surface 33 which permits the apparatus 30 to mate with one or more vertebral bodies. The patient specific surface 33 can be specific to any portion of the patient's anatomy, such as lamina, transverse processes, articular processes, spinous processes, occipital bone, cephalad, etc. Examples are shown in FIGS. 13A-C but expressly understood as being exemplary and not limiting on the scope of the present disclosure.

In embodiments, the registration markers M may be interconnected to a frame or other surgical apparatus that is positioned against the patient's anatomy. Surfaces of the frame may be adapted to at least partially hook around a portion of the patient's anatomy. For example, the patient-contacting surfaces of a frame may comprise multiple portions that are adapted to contact two different planes formed by two distinct portions of the patient's anatomy. In this manner, the surfaces provide a reference to align the frame with a predetermined portion of the patient's anatomy and ensure stability of the frame prior to inserting markers M in the boney anatomy.

A single apparatus 30, which may be referred to as a guide, may target one portion of the lamina. Alternatively, the guide 30 may be sized to facilitate a procedure targeting more than one portion of the patient's anatomy, including, for example, both sides of the lamina substantially simultaneously. In other embodiments the guide 30 may contact the iliac or sacrum or other boney anatomical features associated with a specific patient. Multiple guides 30 may be connected together. Alternatively, a particular guide 30 may be comprised of multiple parts that are selectively interconnectable to form the single guide, and thereby permit use of the guide 30 in a minimally invasive surgical procedure. Certain guides 30 may accommodate multiple registration markers M, without the need to place additional guides.

In embodiments, the patient-specific apparatus, as described herein, may be used in conjunction with particular robotic, navigational or motion control systems, including systems pertaining to fixation-related surgeries. For example, the embodiments shown in FIGS. 15-20 may be used in conjunction with an autonomous or semi-autonomous system for assisting with a particular surgical procedure. More specifically, these embodiments of FIGS. 15-20 may be used in conjunction with devices that employ automated or semi-automated manipulation. Embodiments of the present disclosure may be designed such that the apparatus may be formed and verified, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. It is expressly understood for purposes of this disclosure that other types of machinery other than rapid prototyping machinery may be employed in the systems and methods described herein, for example, by computerized numerical control (CNC) machinery.

Figure 15:
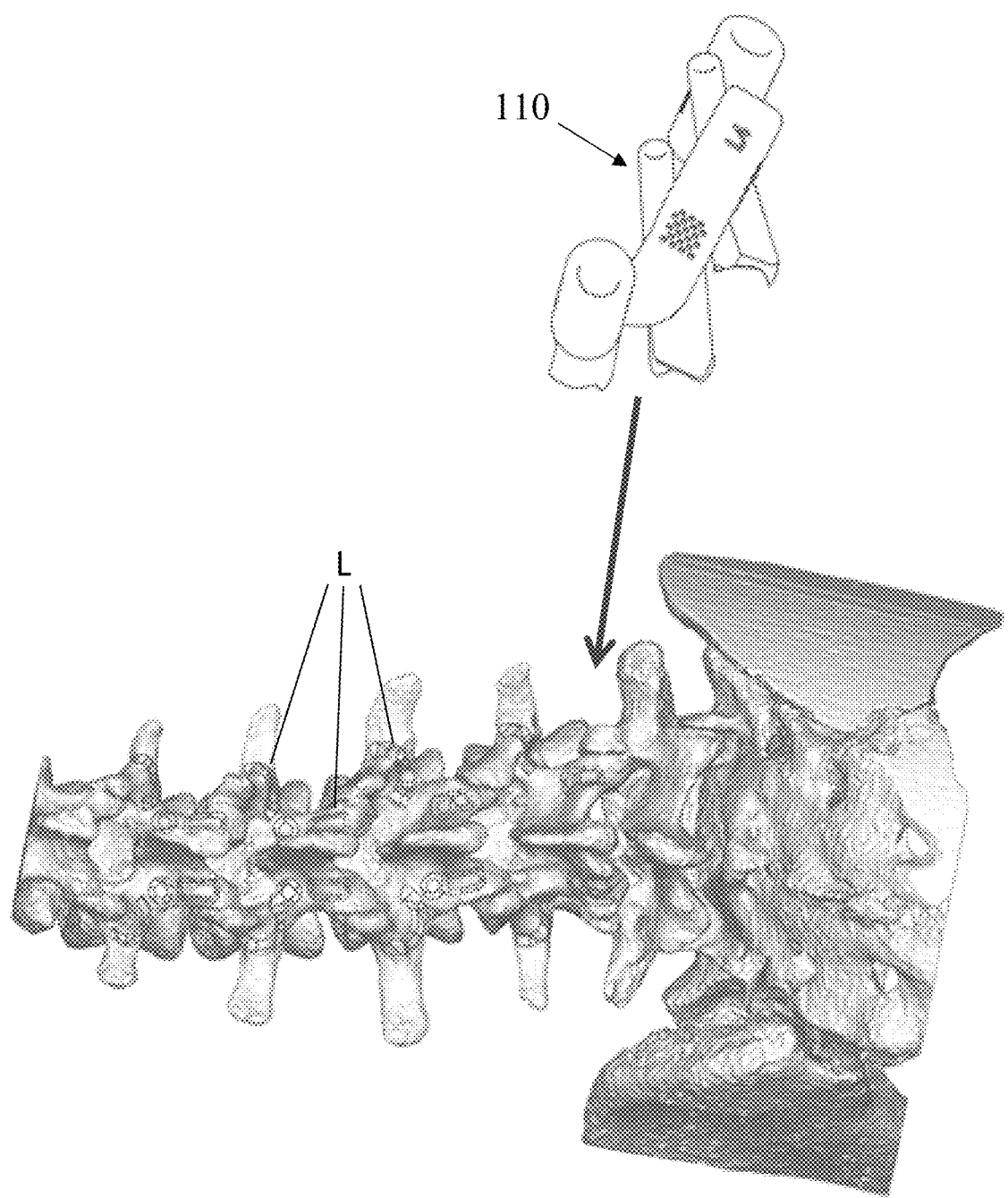
FIG. 15 is a perspective view of a guide used in conjunction with a virtual or augmented reality system.

The patient-specific apparatus, as described herein, may be used in conjunction with particular robotic, navigational, motion control or AR systems, including systems pertaining to fixation-related surgeries. For example, the guide 110 shown in FIGS. 15-16 may be used in conjunction with an AR system for assisting with placement and orientation of a guide, including but not limited to the other patient-specific or patient-matched guides 10, 30 described herein, during a particular surgical procedure. Referring first to FIG. 15, one or more patient contact locations L may be visualized by a surgeon or other health professional by use of the AR system, in particular, by use of wearable devices associated with the AR system. These contact locations L may be displayed to a surgeon or other user as silhouettes or boundaries through the AR system, or otherwise representative of the locations where a patient-specific guide 110 will contact the patient. There may be several contact locations L displayed depending on the complexity of the surgical procedure.

The AR system may be employed with a physical guide 110 adapted to be placed in at least one of the contact locations L displayed by the AR system. One advantage to having a physical guide 110 for use in conjunction with the AR system is that the physical guide may 110 work regardless of movement between individual anatomical features, whereas use of a purely "virtual" system alone may not be accurate, particularly when there is movement following initial registration. Physical guides 110 used in a surgical procedure will still have an image generated from patient-imaging data captured during the surgery, and may be loaded into the AR's software or other configuration program for viewing by the surgeon.

The AR system of this embodiment may be utilized in conjunction with the one or more patient-specific guides 110 to ensure proper alignment of the guides with the patient's anatomy, where contact locations of the guide will display on the actual boney anatomy so the surgeon can align the physical guide 110 with the contact locations. Knowing the correct guide placement (of the physical guide) helps ensure adequate cleaning of soft tissue around the contact locations.

Figure 16:
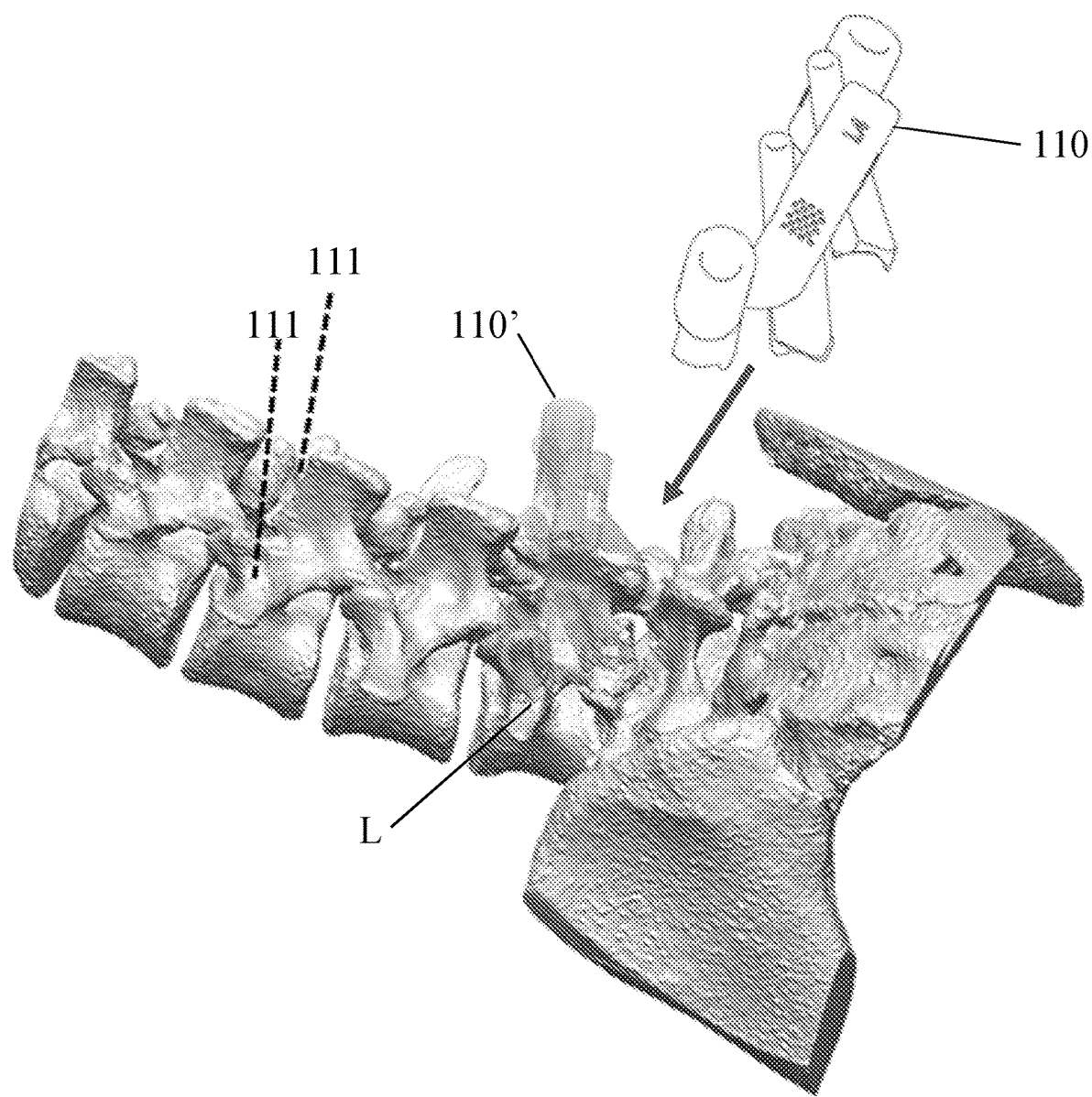
FIG. 16 is another perspective view of a guide used in conjunction with a virtual or augmented reality system.

Referring now to FIG. 16, the AR system may display an image of one or more physical guides virtually 110', such as by depicting a ghosted or shadowed image of the physical guide 110 positioned in the proper placement relative to the patient's anatomical features and the locations L. The surgeon may then utilize this imaging of a virtual guide 110' provided by the AR system to navigate the physical guide 110 to the same location(s) L as indicated by the virtual image 110' of the guide. Additional "shadowed" or virtual guides 110' may appear once the surgeon completes the process for a particular set of contact locations L, for example, by moving to a different vertebral level. It is to be expressly understood that any of the guides 10, 30, 110 may be used in conjunction with the AR system described herein, regardless of whether those guides are pedicle screw guides, lateral mass screw guides, occipital guides, etc.

In addition, one or more trajectories 111 may be displayed by way of the AR system, including through an associated peripheral imaging device, including those described below. These trajectories may be displayed with different indicia, colors, shapes or styles to indicate points of distinction from one trajectory and another trajectory, or alternatively the order or sequence of the trajectories. In this manner, the surgeon may utilize the one or more trajectories 111 for guiding, for example, an instrument or an implant to the precise location shown by the imaging device.

The AR system may further comprise a peripheral imaging device, such as a headset or other wearable device, to permit the surgeon or other health professional view the images displayed by, for example, an associated AR program. Additional devices, such as handheld devices, voice activated devices, headphones, speakers, microphones, haptic devices and controls, holographic imaging equipment, visual displays (including without limitation on-glass display technologies such as Google Glass), and other components provided with AR systems may be supplied to facilitate the objectives described above. In this regard, U.S. Patent Publication Nos. 2020/0092462, 2020/0089314 and 2020/0082621, as well as Applicant's U.S. Pat. No. 10,580, 268 are hereby incorporated by reference in their entireties for the purpose of supplementing this disclosure, pursuant to 35 U.S.C. § 112.

In embodiments, the AR system may also display pre-surgically or post-surgically planned trajectories and/or cutting planes so that a surgeon can align actual instrumentation with the planned procedure, whether that procedure includes insertion of an instrument or implant or a cutting or removal operation. These trajectories of insertion or path of cuts may be virtually projected (similar to the projection of locations on the patient's boney anatomy referred to in FIGS. 15-16) in a plane extending away from the patient's boney anatomy so that a surgeon can clearly see the intended path or placement of instrumentation. In this embodiment, the use and placement of a physical guide (and its associated mechanical constraints) helps to ensure proper pathway is followed.

In embodiments, the AR system described herein may facilitate placement of interbody devices or other implantable devices. The system may be employed to ensure proper placement of plates, plates and rods, or rods alone, including the proper arcuate shape and any necessary bending of the rods used in a particular surgical procedure. The system may be used both pre-surgically and during the surgical procedure, as new registration and/or visualization data is captured by the system. For example, the system may be used for visualizing and executing planned osteotomy cuts or drilling of holes in the patient's boney anatomy, wherein the display of the system shows what areas and/or segments of bone need to be removed to make pre-surgically planned correction. As another example, the system may be used to show and facilitate execution of planned sagittal alignment (to aid in rod bending), or to show planned bone correction to help surgeon achieve desired amount. This example may be used to facilitate procedures on the patient's cervical spine as well.

The AR system described herein may also be configured to indicate where areas of critical anatomy are located (e.g. abdominal aorta, spinal cord, existing nerve roots), including those areas that are sought to be avoided. In this manner, the surgeon may be notified when an instrument or implant (or other device) is approaching a sensitive area to prevent injury. For example, when drilling a pilot hole, the AR system may be configured to compare the planned trajectory with the actual trajectory during the course of the surgical procedure and alert the surgeon that the trajectory deviates (e.g., becomes too medial/inferior/lateral/superior) from the planned trajectory. The use of alerts in this manner may also apply to osteotomy cuts, instrument depth, etc. so that if the course of the surgical procedure does not closely match the planned procedure, the system will provide an alert and recommended correction. In certain embodiments, this deviation may be preset by the surgeon (e.g., by 5-8% or by a preset distance).

In still other embodiments, the system is configured to automatically send alerts when the actual procedure approaches one of the sensitive landmarks or deviates from the planned procedure. In still other embodiments, the system may display locations to avoid during the surgical procedure, such as a defined negative space relative to the targeted surgical site, or alternatively display radiation safe zones in a surgical suite or operating room, for example in relation to a C-arm. The system may also be configured to display sterile environments/instrumentation and send alerts if there is a change in state during a procedure. For example, if something is dropped or comes into contact with a non-sterile environment, the system could automatically change its display state to "non-sterile" or provide an equivalent alert.

In this manner, a surgeon may attach a patient-specific apparatus 110 to each level of the patient's spine that is impacted by a particular surgical procedure, and thereby provide markers for registration and orientation without having to rescan the patient throughout the surgery. In turn, the robotically guided surgical device may view the patient through the markers M and align instrumentation controlled by the robotic equipment. This alignment may be achieved by any one of a combination of guides/markers/patient-specific orientation guides described herein.

Furthermore, the physical apparatus 10, 30, 110 described herein may be provided with embedded locating/information markers. Thus, when the sleeves are inserted into a patient matched guide, the robotic device(s) may orient robotically controlled instruments relative to the drill sleeves location and embedded information on each level a guide is present. In certain embodiments, such as with a prior fusion procedure, only one guide/locating marker would be needed. In some embodiments, the apparatus is 3D printed with metal or plastic material. In other embodiments, the apparatus is fabricated using one of the other methods described herein.

Autonomous and semi-autonomous systems may further comprise an adjustable, robotic arm assembly, which may be affixed to a piece of machinery, an operating surface or alternatively to the patient. The arm assembly may substantially facilitate the placement of surgical screws during spinal surgeries by securing the guide and corresponding coupling devices to a stationary surface, thereby providing greater stability and, in turn, more accurate placement of screws and/or other fixation devices. For example, a patient specific guide may be engaged with the corresponding patient specific anatomy of a desired surgical site. An adjustable arm assembly, which is secured to a stationary surface, such as an operating or side table or other surface, can then engage the guide via corresponding coupling devices to provide greater stability and delivery of fixation devices therethrough. This attachment between the device(s) and the arm assembly may permit a user to set and fix, for example, the sagittal angle of the device(s) when performing a surgical procedure on the patient's spine.

One having skill in the art will appreciate that embodiments of patient specific guides, as well as other embodiments discussed herein, may be used in conjunction with devices that employ automated or semi-automated manipulation, such as, for example, robotics, image guidance or other autonomous systems. Embodiments of patient specific guides may also be designed such that the guide may be operated and verified, in whole or in part, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. These apparatus and systems may be programmed to operate with the patient-specific guides, the same having known dimensions and therefore provide ease of validation and operation by automated or semi-automated means.

In one embodiment discussed above, for example, the adjustable arm assembly may be associated with, or controlled by, a robot, programmable apparatus, CNC machinery or equivalent equipment used to perform a surgical procedure. In other embodiments, the guide may be configured for use in conjunction with or to further supplement the use of a navigation device. More specifically, autonomous placement of the patient specific guide via the adjustable arm assembly with the corresponding anatomical feature(s) of the patient assists with one or more of registration, stability, and motion tracking. The navigation device coupled with the adjustable arm assembly and/or patient-specific guide may optionally track the position of instruments, equipment or hardware in relation to the patient's anatomy during a surgical procedure. Accordingly, the navigation device may display positions of instruments, equipment or hardware as they are used during the surgical procedure. In yet other embodiments, the placement of the guide may supplement the registration, stability and motion tracking features provided by the navigation device. In these embodiments, such surgical procedures may be entirely or partly performed via autonomous or semi-autonomous systems and methods so as to limit the exposure of certain harmful or toxic chemicals or transmissions (e.g., radiation) to the surgeon and other attending medical staff. Such autonomous and semi-autonomous systems and methods may also substantially increase the speed and accuracy of the surgical procedure.

FIGS. 17-18 demonstrate another embodiment of the present disclosure. Referring specifically to FIG. 17, a patient-specific apparatus 110 may be provided that comprises one or more legs 112 and/or one or more alignment channels 114, but preferably no cannula. This apparatus 110 comprises at least two surfaces 116 that are patient-specific or patient-matching and designed to contact the patient in two unique locations, such as locations found on a single vertebral level. The apparatus 110 preferably includes at least one integrated registration marker M for use in conjunction with robotic navigation and or autonomous/semi-autonomous systems described herein. In certain embodiments, the registration marker M is removable and/or positionable according to the surgeon's desire and the presurgical plan. Alternatively, the registration marker(s) M may be embedded into the apparatus 110 and affixed in such a manner to prevent manipulation. The patient-specific apparatus 110 may further comprise indicia 115 to assist with associating the apparatus 110 with the patient-matching surfaces or features, or to identify a particular level of a patient's vertebrae.

According to another embodiment shown in FIG. 18, a patient-specific guide 110 may comprise cannula(e) 118 that are capable of receiving a sleeve or insert 120 within the hollow opening of the cannula 118. In this embodiment, a sleeve or insert 120 may comprise an embedded marker M, chip, circuit, or equivalent, in order to convey registration and instructions to a computer-aided piece of equipment, such as a robotic device. In this manner, a patient-specific guide 110 may have patient-contacting surfaces 116 specific to a particular patient's boney or other anatomy and placed in the corresponding anatomical locations the guide 110 is designed to mate with. Then, a specific insert 120 may be placed in one or more cannula(e) 118 of the guide 110 for location by the robotic or other autonomous equipment. When completed, the guide 110 may be removed, or alternatively the registration marker(s) M may be removed. Several different styles of registration markers M, chips, circuits, etc. may be employed using this particular embodiment.

By way of example, several of the guides 110 shown in FIGS. 17 and 18 may be placed along the patient's spine, in distinct vertebral locations, and thereby provide the user with the ability to register various locations for surgical planning or, in certain embodiments, robot-assisted navigation. More specifically, several patient-specific guides 110 described herein may be used with various orientation or registration markers M for identification by a robot. Certain guides 110 may comprise an embedded chip, circuit or equivalent, which contains presurgical planning information, and which may be read by a machine and deliver specific instructions to a robotic surgical device, for example. In this manner, a surgeon may attach a patient-specific apparatus 110 to each level of the patient's spine that is impacted by a particular surgical procedure, and thereby provide markers M for registration and orientation without having to rescan the patient throughout the surgery. In turn, a computer-aided navigational device or equivalent may view the patient through the markers M and align instrumentation controlled by the robotic equipment.

Although in one embodiment these guides remain in place during surgery, in another embodiment the guides may be applied and removed as necessary for the surgeon to register the robotic equipment with patient anatomy, in spite of any intersegmental motion occurring during the surgical procedure. This alignment may be achieved by any one of a combination of guides/markers/patient-specific orientation guides.

Referring now to FIGS. 19A-20B, an additional embodiment is shown. Here, a patient-specific apparatus 140 may be provided that attaches to a specific feature or portion of a patient's anatomy. This guide 140 is preferably low profile, such that it rests close to the patient's anatomy. The guide 140 also preferably comprises at least three distinct surfaces 146 that are patient-specific and designed to contact the patient in unique locations, although in other embodiments the guide 140 may comprise more or fewer than three such surfaces. In this embodiment, and referring to FIGS. 19B and 20B, the guide 140 is configured to match a patient's vertebra.

Figure 19A:
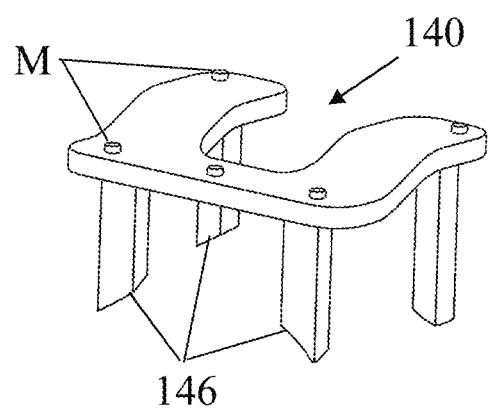
FIGS. 19A-B are various views of another guide and marker(s) according to embodiments of the present disclosure.
Figure 19B:
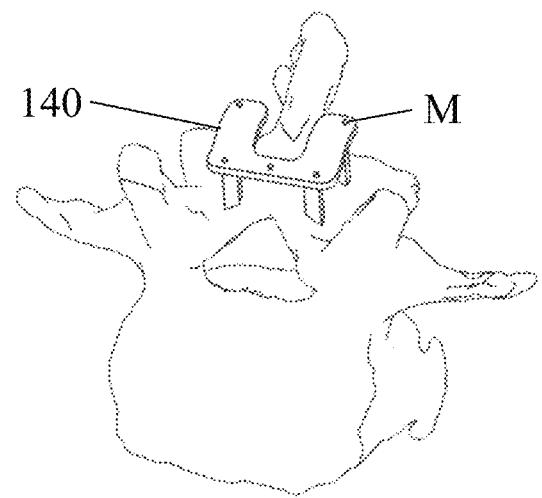
Figure 20A:
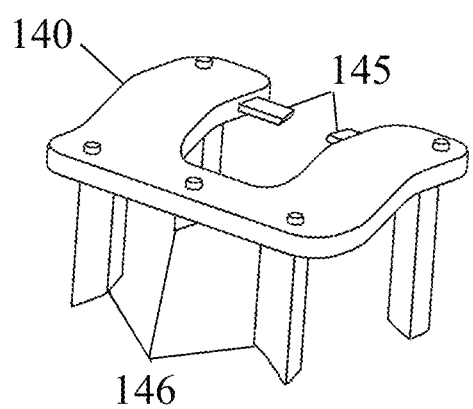
FIGS. 20A-B are various views of yet another guide and marker(s) according to embodiments of the present disclosure.
Figure 20B:
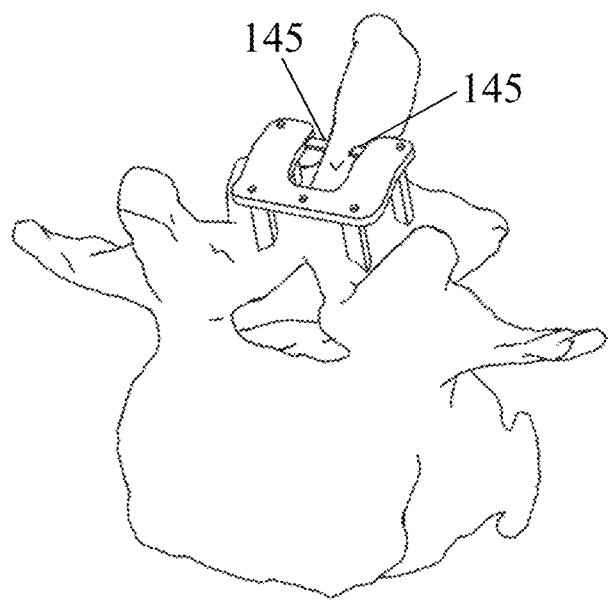

This embodiment is intended to demonstrate an exemplary low-profile apparatus, which may remain in place during a surgical procedure without obstructing the surgeon's field of view or interfere with use of surgical instrumentation. As shown in FIGS. 19A and 20A, the guide 140 may include one or more registration markers M, such as for identification by a robot or other computer-controlled navigation equipment. In embodiments, guides 140 may further comprise an embedded gyroscope, chip, circuit or equivalent with presurgical planning information, which may be read by a robot or computer-aided machine to deliver specific instructions to automated and/or autonomous surgical equipment. Embedded features, including the registration markers M, may transmit information regarding the position of the vertebral body compared to the presurgical plan in order for the robotic device to re-calibrate itself in the event of intersegmental motion.

The guide 140 according to this embodiment may comprise contact features which help keep the guide 140 securely in place. For example, the guide of FIGS. 20A-B comprises surfaces or projections 145 that contact, for example, the spinous process to direct and secure the guide 140 in position. In addition, several patient-specific guides (as described herein) may be used with their corresponding orientation or registration markers M (or other embedded features described above) for identification by a robot or other navigation equipment for use in, for example, a multi-level surgical procedure. As described above, these embedded features may transmit information regarding the position of the vertebral body compared to the presurgical plan in order for the robotic surgical device to re-calibrate itself in the event of intersegmental motion. In this manner, a surgeon may attach a patient-specific guide 140 with unique registration markers M to each level of the patient's spine that is impacted by a particular surgical procedure, and thereby provide markers M for registration and orientation. This in turn eliminates the need to rescan the patient throughout the surgery and, in turn, the robotic device may view the patient through the markers M and align instrumentation controlled by the robotic equipment specific to those registration points. This alignment may be achieved by a combination of markers M/patient-specific orientation guides 140.

The distinct patient-contacting surfaces or projections 146 may be adapted to fit directly to aspects of the patient's anatomy, such as one or more of the medial side of the inferior articular process, the lateral sides of the lamina, the spinous process, and the junction between the pars and the transverse process, the iliac, the sacrum, or other anatomical features of the patient. The projections 145 may optionally contact at least a portion of the spinous process. These surfaces are preferably determined to match at least a portion of a curvature of the patient's anatomy to facilitate placement of the guide 140 in a predetermined alignment with respect to a predetermined portion of the patient's anatomy during a surgical procedure. These surfaces may be matched to substantially conform to a predetermined portion of the patient's anatomy as described herein.

In one embodiment, the guides described herein are designed following acquisition of a scan of the patient's anatomy with a medical imaging device. The scan may be performed by a CT scanner, an MRI scanner, or any other medical imaging device. The scan is segmented into 3D models of each vertebra. These 3D models are then modified in CAD to simulate the correction desired by the surgeon. Once the desired correction is appropriately simulated, a guide is generated that will allow the surgeon to make the planned corrections intraoperatively. The guides may then be manufactured through 3D printing, rapid prototyping, or an alternative method for creating patient-specific features.

The guides of the present disclosure can be used as physical cutting guides, drill guides, bone removal guides, implant guides, screw guides, instrument guides or guides for other surgical equipment or instrumentation. Additionally, the guides may be used as an aid to indicate to surgeons the angle and location of drilling or cuts so that neural elements in the patient's spine are not harmed. The guides may also be used pre-surgically on models of the patient's anatomy to test or practice the planned surgical procedure. At least a portion of the proximal end of the guide is configured to extend outside of the patient during a surgical procedure.

Various apparatus formed by the system and method described above may be used for a particular fixation related surgery. The guides described herein may be used for navigation of one or more of a cortical bone trajectory, a pedicle screw trajectory, an occipital trajectory, or other trajectories in the spine of a patient.

In one embodiment, at least a portion the guide is reusable. Optionally, at least a portion of the guides projects beyond the patient's anatomy when in a position of use during a surgical procedure. For example, at least a proximal portion of a cannulae of one or more of the guides may project from an incision formed during surgery.

Additionally, the patient-specific guides may comprise individual pieces that are adapted to be assembled by a surgeon before, or during, a surgical procedure. The portions or components of the guides may be disassembled and delivered to a specific area of the patient's anatomy for assembly during the surgical procedure. For example, the medial bodies, cannulae, and legs of the guides may pass through a bore of a cannula of another tool and assembled during a minimally invasive surgical procedure.

The cannula described herein may be configured to contact, by way of example but not limitation, one or more of the lamina, pars interarticularis, aspects of the transverse process, the interior articular process, and the superior articular process of the patient. Cutouts (not illustrated) may be formed on a portion of the cannulae to prevent the guide from contacting the spinous process of the patient, adjacent vertebrae, or to avoid other patient anatomy.

The cannulae may have a generally cylindrical shape but other shapes are contemplated. Each of the two cannulae may have a unique orientation and size. The cannulae may be of any length and differ from one cannula to another cannula provided with the apparatus, based at least in part on the specific patient's anatomical features, preferences of the surgeon, orientation of the guide, and the type of tool or fixation device associated with the cannulae. The length of the cannulae may also be selected to provide depth control of instruments guided by the cannulae. For example, in one embodiment, the cannulae has a first length to allow a drill bit to penetrate a first depth into the patient's anatomy. In another example, the cannulae has a second length that is greater than the first length. Accordingly, the cannulae prevents the drill bit from penetrating the first depth into the patient's anatomy.

The cannulae may optionally include extensions of any size or shape. In one embodiment, the extensions are positioned proximate to a distal end of the cannulae. In another embodiment, the extensions wrap at least partially around the exterior of the cannulae. The extensions may also project at least partially beyond the distal end of the cannulae. The extensions are adapted to wrap at least partially around a predetermined portion of the patient's anatomy. In one embodiment, the extensions are adapted to wrap around a portion of one of the pars and the superior articular process.

In one embodiment of the present disclosure, the bore of the cannulae may facilitate and guide a drill bit, or any other suitable instrument to drill and tap a pilot hole in the cortical trajectory. After the pilot hole is created, the bore may further guide insertion of a fixation device, such as a cortical screw, into the pilot hole. In another embodiment of the present disclosure, the bore may be adapted to receive one or more inserts or guide wires such as the inserts.

Various benefits achieved from the use of these patient-specific guides include: providing means to achieve quick and controlled removal of bone; providing spatial orientation of cutting tools used during the procedure; ensuring correct orientation, both through controlled guiding of the instrument and visualization during the pre-surgical planning process; providing accurate calculation of deformity correction, prior to operating; providing accurate bone resection, which in turn ensures deformity correction; depth controlled or hard stop restrictions to protect neural and vascular elements; controlled cutting or insertional vectors and avoiding contact or injury to neural elements; and ability to provide approach for cuts or implantation in a posterior, anterior, posterior lateral, transforaminal or direct lateral approach.

Additionally, the guides described herein facilitate quicker bone removal and instrumentation of the patient's boney anatomy, decreasing surgical time and associated risk to the patient. These guides also increase the accuracy of procedures performed using the guide by providing patient matched surfaces to conform to a predetermined alignment of the guide with respect to the patient's anatomy. In this manner, the guides decrease the amount of fluoroscopy required to verify or correct the alignment of the guide, decreasing radian expose to medical staff as well as the patient.

Although embodiments are described and in certain figures shown as one piece, it will be appreciated that in other embodiments the guide could include multiple pieces or a series of guides that are placed in a specific order to generate a series of operations or actions. In embodiments of guides comprising multiple pieces, each piece of the guide may be keyed to interconnect in a specific order and location to other pieces of the guide. In one embodiment, the guide does not contact the patient's anatomy. In another embodiment, at least a portion of the guide is adapted to contact the patient's anatomy.

Although the devices described above have been illustrated for use with certain guide screws and/or instruments, it is expressly understood that the devices may be used with a variety of other implantable and non-implantable apparatus, including by way of example, medial-to-laterally placed transpedicular screws (commonly referred to as cortical bone trajectory screws). Other screws and instruments may be used with the surgical devices described above without departing from the spirit of the disclosure and are considered to be within the scope of the appended claims.

The apparatus described herein may facilitate the introduction of Kirschner wire (K-wire) that may be visualized through various imaging systems known in the art, and which may further be used to identify a desired patient-specific marker or location. Such procedure may also allow for successful dilation through the introduction of sequential muscle or soft tissue dilators, which may allow for a quicker, more effective operation. The use of such apparatus, as discussed above, may also prevent the need of additional surgical devices, such as multiple retractors of various sizes, which may substantially reduce the logistics and cost of preparation of an operation.

Other embodiments of the present disclosure may include patient specific insertional guides that may include patient-specific contours or channels that conform to anatomical markers. Such patient specific insertional guides may be used for the placement of external hardware or guide surgical equipment or instrumentation for percutaneous and/or subcutaneous introduction, which may be predetermined using medical imaging and/or computer aided design software as described in conjunction with the systems and methods disclosed herein. In such procedures, the external hardware and/or surgical equipment may be guided via the patient-specific contours or channels by location, axes and/or insertional trajectories, and/or depth to substantially ensure accuracy. In these embodiments, hardware or instrumentation is substantially guided during surgery via predetermined patient-specific anatomical markers on a surgical area of interest. Said another way, at the time of surgery the guide may be placed at a predetermined surgical location, either percutaneously or subcutaneously, that can then direct and facilitate the operation by way of accurate introduction of external hardware or guided surgical equipment or instrumentation. Such procedures may also substantially guarantee the safety and reliability of the procedure.

The models, templates and other patient-specific or patient-matched apparatus described herein may be manufactured by any known method of manufacture, or by methods developed after the date of this disclosure. In one embodiment, models are manufactured using a rapid manufacturing process such as 3D printing, although other processes are contemplated. The models can be fit to the patient's anatomy during surgery to help the surgeon visualize the correct angles and starting locations for cuts, inserting drills or other surgical instruments, or introducing an implant, such as a plate or screw. In one embodiment, the models include at least one cannula. The cannula(e) may be adapted to receive fixtures to at least temporarily interconnect the model to portions of the patient's anatomy. Fixtures may also be received in the cannula to interconnect portions of a modular model together.

One having skill in the art will appreciate that embodiments of patient specific guides, as well as other embodiments discussed herein, may be used in conjunction with devices that employ automated or semi-automated manipulation, such as, for example, robotics, image guidance or other autonomous systems. Embodiments of patient specific guides may also be designed such that the guide may be operated and verified, in whole or in part, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. These apparatus and systems may be programmed to operate with the patient-specific guides, the same having known dimensions and therefore provide ease of validation and operation by automated or semi-automated means.

In one embodiment discussed above, for example, the adjustable arm assembly may be associated with, or controlled by, a robot, programmable apparatus, CNC machinery or equivalent equipment used to perform a surgical procedure. In other embodiments, the guide may be configured for use in conjunction with or to further supplement the use of a navigation device. More specifically, autonomous placement of the patient specific guide via the adjustable arm assembly with the corresponding anatomical feature(s) of the patient assists with one or more of registration, stability, and motion tracking. The navigation device coupled with the adjustable arm assembly and/or patient-specific guide may optionally track the position of instruments, equipment or hardware in relation to the patient's anatomy during a surgical procedure. Accordingly, the navigation device may display positions of instruments, equipment or hardware as they are used during the surgical procedure. In yet other embodiments, the placement of the guide may supplement the registration, stability and motion tracking features provided by the navigation device. In these embodiments, such surgical procedures may be entirely or partly performed via autonomous or semi-autonomous systems and methods so as to limit the exposure of certain harmful or toxic chemicals or transmissions (e.g., radiation) to the surgeon and other attending medical staff. Such autonomous and semi-autonomous systems and methods may also substantially increase the speed and accuracy of the surgical procedure.

Reference to terms such as "imaging device" or equivalent peripherals are intended to include any type of device capable of communicating with one or more of another device and/or across a communications network, via a communications protocol, and the like. Exemplary communication devices may include but are not limited to smartphones, handheld computers, laptops, netbooks, notebook computers, subnotebooks, tablet computers, scanners, portable gaming devices, phones, pagers, GPS modules, portable music players, and other Internet-enabled and/or network-connected devices.

Communication or transmission of information, as described herein, may be achieved through a variety of modalities and/or protocols, or specific communication sessions or interactions, such as Voice-Over-Internet-Protocol ("VoIP), cellular communications (e.g., IS-95, 1G, 2G, 3G, 3.5G, 4G, 4G/IMT-Advanced standards, 3GPP, WIMAX™, GSM, CDMA, CDMA2000, EDGE, 1xEVDO, iDEN, GPRS, HSPDA, TDMA, UMA, UMTS, ITU-R, and 5G), Bluetooth™, text or instant messaging (e.g., AIM, Blauk, eBuddy, Gadu-Gadu, IBM Lotus Sametime, ICQ, iMessage, IMVU, Lync, MXit, Paltalk, Skype, Tencent QQ, Windows Live Messenger™ or MSN Messenger™, Wireclub, Xfire, and Yahoo! Messenger™), email, Twitter (e.g., tweeting), Digital Service Protocol (DSP), and the like.

The term "network" and variations thereof, as used herein, can refer to a collection of communication components capable of one or more of transmission, relay, interconnect, control, or otherwise manipulate information or data from at least one transmitter to at least one receiver. As such, the network may include a range of systems supporting point-to-point or broadcasting of the information or data. A system may refer to the collection individual communication hardware as well as the interconnects associated with and connecting the individual communication hardware. Communication hardware may refer to dedicated communication hardware or may refer a processor coupled with a communication means (i.e., an antenna) and running software capable of using the communication means to send and/or receive a signal within the communication system. Interconnect refers some type of wired or wireless communication link that connects various components, such as communication hardware, within a communication system. A communication network may refer to a specific setup of a communication system with the collection of individual communication hardware and interconnects having some definable network topography. A communication network may include wired and/or wireless network having a pre-set to an ad hoc network structure.

The term "computer-readable medium," as used herein refers to any tangible storage and/or transmission medium that participates in providing instructions to a processor for execution. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a compact disc read only memory (CD-ROM), any other optical medium, punch cards, paper tape, any other physical medium with patterns of holes, a random access memory (RAM), a programmable read only memory (PROM), and erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. It should be noted that any computer readable medium that is not a signal transmission may be considered non-transitory.

The term "module" as used herein refers to any known or later developed hardware, software, firmware, artificial intelligence, fuzzy logic, or combination of hardware and software that is capable of performing the functionality associated with that element.

The terms "determine," "calculate," and "compute," and variations thereof, as used herein, are used interchangeably and include any type of methodology, process, mathematical operation, or technique.

The terms "communicating" or "in communication with," as used herein, refers to any coupling, connection, or interaction using electrical signals to exchange information or data, using any system, hardware, software, protocol, or format, regardless of whether the exchange occurs wirelessly or over a wired connection.

Each of the guides described herein can interface with any vertebra level or more than one vertebra level, including without limitation the cervical spine. Further, each of the guides preferably include at least one cannula. The cannula (e) may include a bore adapted to guide one or more guide wires, drill bits, taps, and screws. Thus, the bore may guide a drill apparatus and/or a fixation device. Optionally, a cannula may be devoid of a bore. The cannula without a bore is adapted to provide stability as other portions of the guide are used in a surgical procedure. Additionally, or alternatively, the guides may comprise secondary and/or tertiary cannulae adapted to guide one or more of the group comprising guide wires, drill bits, taps, screws, couplings, and other instrumentation including without limitation tools adapted to harvest bone grafts. The cannulae may be of a variety of lengths. In one embodiment, at least a portion of the proximal end of the cannulae and the guide is configured to extend outside of the patient during a surgical procedure.

In one embodiment, at least a portion the guide is reusable. Optionally, at least a portion of the guides projects beyond the patient's anatomy when in a position of use during a surgical procedure. For example, at least a proximal portion of a cannulae of one or more of the guides may project from an incision formed during surgery.

Other benefits achieved from the use of these patient-specific guides include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

Additionally, the patient-specific guides may comprise individual pieces that are adapted to be assembled by a surgeon before, or during, a surgical procedure. The portions or components of the guides may be disassembled and delivered to a specific area of the patient's anatomy for assembly during the surgical procedure. For example, the medial bodies, cannulae, and legs of the guides may pass through a bore of a cannula of another tool and assembled during a minimally invasive surgical procedure.

The cannulae may have a generally cylindrical shape but other shapes are contemplated. Each of the two cannulae may have a unique orientation and size. The cannulae may be of any length based at least in part on the specific patient's anatomical features, preferences of the surgeon, orientation of the guide, and the type of tool or fixation device associated with the cannulae. The length of the cannulae may also be selected to provide depth control of instruments guided by the cannulae. For example, in one embodiment, the cannulae has a first length to allow a drill bit to penetrate a first depth into the patient's anatomy. In another example, the cannulae has a second length that is greater than the first length. Accordingly, the cannulae prevents the drill bit from penetrating the first depth into the patient's anatomy.

In one embodiment of the present disclosure, the bore of the cannulae may facilitate and guide a drill bit, or any other suitable instrument to drill and tap a pilot hole in the cortical trajectory. After the pilot hole is created, the bore may further guide insertion of a fixation device, such as a cortical screw, into the pilot hole. In another embodiment of the present disclosure, the bore may be adapted to receive one or more inserts or guide wires such as the inserts.

Although not illustrated in the appended drawing figures, the guide may further comprise attachment points formed in one or more of the medial body, the cannulae, and the legs. The attachment points are adapted to receive one or more secondary or tertiary cannulae. The cannulae may include a bore or a cutting slot to guide an instrument to target another portion of the patient's anatomy. In one embodiment, the cannulae are adapted to target one or more predetermined portions of the cervical spine (i.e., C1-S1 and ilium).

In one embodiment, the attachment points comprise slots to receive extensions of the cannulae. In one embodiment, the slots may also direct the path of a blade or other cutting instrument, or to receive a measurement aid or tool for facilitating the surgeon/user in identifying landmarks, surrounding boney anatomy, placement of implanted devices, or for surgical planning.

The guide may also include indicia to identify a sequence of use or portions of the patient's anatomy with which the guide is to be used. The indicia may also indicate a tool to be used, a direction of a cut to be performed, or a planned orientation or alignment of the guide. According to one embodiment, the guide may further comprise one or more indicia for identifying the guide with a particular patient.

The patient specific surfaces may include any number of protrusions, depressions, and contours to substantially conform to the patient's anatomy. For example, the patient specific surfaces may comprise multiple portions that are adapted to contact two different planes formed by two distinct portions of the patient's anatomy. The patient specific surfaces are adapted to one or more of: align the insert in a predetermined position with respect to the patient's anatomy; hook around a portion of the patient's anatomy; prevent unintended or inadvertent movement of the insert during a surgical procedure; and displace soft tissue. In one embodiment, the patient specific surfaces comprise relatively thin extensions to displace soft tissue. By protruding at least partially around and substantially conforming to different portions of the patient's anatomy, the patient specific surfaces generally "hook" at least partially around (or to) the patient's anatomy. Thus, the surfaces may contact at least two different planes formed by distinct surfaces of the patient's anatomy. Accordingly, the insert is adapted to at least partially fit and substantially conform to predetermined portions of one or more vertebrae during the surgical procedure.

The patient specific surfaces help position the guide and keep it in position in a predetermined position and orientation. The combination of patient specific surfaces formed on various locations of the insert may decrease the possibility of improper placement of the interbody guide in relation to the patient's anatomy. The surgeon may also receive tactile feedback when advancing the insert between two adjacent vertebrae, such as a clip, snap, or vibration when the insert is properly aligned with, and received between, the vertebrae.

The projections may also be adapted to bias into a predetermined orientation with respect to the patient's anatomy. Accordingly, the material of the insert may be selected to allow a surgeon bend or stretch to hook around the patient's anatomy. In one embodiment, the insert or portions thereof, may be manufactured from a material that is at least partially flexible or deformable. In another embodiment, the insert is manufactured from a material with shape memory, such as Nitinol. In this manner, when properly aligned with the patient's anatomy as planned, the insert may be releasably retained in a predetermined alignment with respect to the patient's anatomy.

Additionally, or alternatively, the projections may be asymmetrical. Thus, in one embodiment, one projection has a shape and/or size that is different than the other projection. For example, one projection may have a different thickness, contour, or length than the other projection. The asymmetric shape or size of the projections may be planned to provide a predetermined correction to the patient's spine. Similarly, the asymmetric projections may be shaped for use with a defect of the patient's spine. Additionally, the angle and orientation of each projection with respect to the distal surface of the insert can be varied to match the anatomy of the patient, or to avoid a portion of the patient's anatomy. In one embodiment, the shape of the projections does not provide correction of deformities of the patient's anatomy. In another embodiment, the shape of the projections provides at least some correction of the patient's deformity. Portions of the projections may have a tapered shape that can be used to distract the vertebrae. For example, the distal portion of each projection may comprise a full-radius or bullet-shaped nose for ease of insertion. Additionally, or alternatively, the distal portions may have a wedge shape.

Screws as described herein may be placed specifically to interconnect the tools to the patient's anatomy. Screws and other implants may also be patient-specific and may be specific to a particular guide as well. For instance, in certain embodiments the screw may have at least a portion that is configured to be received within a bore of at least one cannula and only advance within the bore if it is the patient-specific screw corresponding to the patent-specific guide that is to be used with the particular screw. The bore may have surfaces that are complementary to the surfaces of the screw or other implant.

Other benefits achieved from the use of these patient-specific interbody guides of all embodiments of the present disclosure include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery. The embodiments also reduce the cumulative radiation exposure to both the surgeon and medical professionals in the operating environment and the patient.

Additionally, the guides facility quicker bone removal and instrumentation of the patient's boney anatomy, decreasing surgical time and associated risk to the patient. The guides also increase the accuracy of procedures performed using the guide by providing patient matched surfaces to conform to a predetermined alignment of the guide with respect to the patient's anatomy. In this manner, the guides decrease the amount of fluoroscopy required to verify or correct the alignment of the guide, decreasing radian expose to medical staff as well as the patient.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

With respect to the embodiments described above, it is expressly understood that such embodiments may be incorporated for use in practicing the novel methods described herein. In certain embodiments, those methods may comprise greater or fewer steps than as described above. By way of example, but not limitation, one step for use with the various embodiments described above may comprise the use of various technologies for capturing a patient's unique morphology, and subsequently mapping and/or planning the fabrication of a device comprising one or more "patient matched" surfaces or features for complementing that unique morphology. Further, such devices may be further optimized with respect to the unique data associated with the patient, such that the device may be matched with specific devices for use during the surgical procedure, or oriented around the patient's own anatomy to achieve, for example, one or more desired insertional trajectories (which may be verified in a pre-operative setting). Variations on this step, and the inclusion or exclusion of additional steps described herein are expressly contemplated by the present disclosure.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

Additionally, although the fusion cages of the present disclosure are particularly well-suited for implantation into the spinal column between two target vertebrae, and although much of the discussion of the present disclosure is directed toward their use in spinal applications, advantages offered by embodiments of the present disclosure may also be realized by implantation at other locations within a patient where the fusion of two or more bony structures may be desired. As one of skill in the art will appreciate, the present disclosure has applications in the general field of skeletal repair and treatment, with particular application to the treatment of spinal injuries and diseases. It should be appreciated, however that the principles of the present disclosure can also find application in other areas.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A customized patient-specific apparatus for use with an augmented reality system, comprising:
   a central portion of the patient-specific apparatus, which comprises a first and a second extension;
   at least a first surface configured to be complementary to a predetermined portion of a patient's boney anatomy;
   at least a second surface distinct from the at least a first surface that is configured to be complementary to another predetermined portion of a patient's boney anatomy;
   at least one marker in communication with the augmented reality system;
   wherein the at least one marker communicates the location and orientation of the apparatus to the augmented reality system; and
   wherein placement of the at least a first surface on the predetermined portion of a patient's boney anatomy and placement of the at least a second surface on the another predetermined portion of a patient's boney anatomy is verified by the augmented reality system through communication with the at least one marker.

2. The apparatus of claim 1, wherein the marker is removable from the apparatus.

3. The apparatus of claim 2, wherein the apparatus further comprises a bore, and wherein the bore is used to guide a tool or instrument to create an aperture in a predetermined portion of a patient's boney anatomy for placement of the at least one marker.

4. The apparatus of claim 1, wherein the at least one marker is selected from the group consisting of a registration marker, a microchip, a circuit, a coil, a gyroscope and an indicia.

5. The apparatus of claim 4, wherein the at least one marker is embedded in the apparatus.

6. The apparatus of claim 1, wherein the at least one marker is selectively engaged within an aperture in the central portion of the apparatus.

7. The apparatus of claim 4, wherein the at least one marker configuration is selected from a group consisting of various orientations, lengths, and sizes.

8. The apparatus of claim 6, wherein the configuration and location of the at least one marker relative to the central portion are communicated to the augmented reality system after the at least one marker is selectively engaged within the aperture.

9. The apparatus of claim 1 further comprising at least a third surface distinct from the at least a first and second surfaces, wherein the at least a third surface is configured to be complementary to a different portion of a patient's boney anatomy than the first and second surfaces.

10. The apparatus of claim 1, wherein at least one planned orientation of the surgical instruments and implants, relative to the at least one marker, is displayed on at least one peripheral device.

11. The apparatus of claim 1, wherein the location and orientation of the apparatus is displayed on at least one peripheral device.

12. The system of claim 11, wherein the at least one peripheral device is selected from the group consisting of a wearable device, a handheld device, a voice activated device, a pair of glasses, a pair of goggles, a set of headphones, a speaker, a microphone, a haptic device, a holographic imaging device, a monitor, a screen, a visual display, an on-glass display and an audible device.

13. An augmented reality system for performing one or more surgical procedures facilitated by a computer-aided navigational apparatus, comprising:
- at least one robotic apparatus;
- a processor in communication with the at least one robotic apparatus;
- a patient-specific apparatus configured to be placed on at least one patient-specific feature;
- at least one marker that is positioned in a known location relative to patient anatomy and configured to transmit positional information to the processor;
- wherein the at least one marker in communication with the augmented reality system;
- wherein the at least one patient-specific feature corresponds to a patient's boney anatomy; and
- wherein the processor is configured to receive and relay the positional information received from the at least one marker to the augmented reality system to determine the location and orientation of the at least one robotic apparatus relative to the patient's boney anatomy.

14. The system of claim 13, wherein the at least one marker is selected from the group consisting of a registration marker, a microchip, a circuit, a coil, a gyroscope and an indicia.

15. The system of claim 13, wherein the marker is embedded in the apparatus.

16. The system of claim 13, wherein the marker is selectively engaged with the apparatus.

17. The system of claim 13, wherein the apparatus further comprises a bore, and wherein the bore is used to guide a tool or instrument to create an aperture in the at least one patient-specific feature.

18. The system of claim 17, wherein the marker is selectively engaged with the aperture.

19. The system of claim 13, wherein the location of the patient-specific apparatus is displayed on at least one peripheral device.

20. The system of claim 19, wherein the at least one peripheral device is selected from the group consisting of a wearable device, a handheld device, a voice activated device, a pair of glasses, a pair of goggles, a set of headphones, a speaker, a microphone, a haptic device, a holographic imaging device, a monitor, a screen, a visual display, an on-glass display and an audible device.

21. The system of claim 13, wherein the patient-specific apparatus comprises at least a first patient-specific surface and a second patient-specific surface, the first and second surfaces configured to be placed on multiple of the at least one patient-specific features.

22. The system of claim 21, wherein the patient-specific apparatus comprises at least a third patient-specific surface.

23. The system of claim 13, wherein the processor is configured to deliver alerts, warnings or other signals based on the location of the at least one marker.

24. The system of claim 23, wherein the alerts, warnings or other signals include an alert when the at least one marker is in an undesired location, and include a different alert when the at least one marker is in a predetermined desired location.

25. The system of claim 13, wherein the robotic device interfaces or connects with the patient-specific apparatus when the apparatus is fit to the patient's boney anatomy, and wherein the robotic device is also oriented to one or more of the patient-specific features.

* * * * *